(12) United States Patent
Abbott et al.

(10) Patent No.: US 9,968,396 B2
(45) Date of Patent: May 15, 2018

(54) SURGICAL INSTRUMENT AND METHOD

(75) Inventors: Ryan Abbott, San Jose, CA (US); Fred Ginnebaugh, Sunnyvale, CA (US)

(73) Assignee: MAQUET CARDIOVASCULAR LLC, Wayne, NJ (US)

( * ) Notice: Subject to any disclaimer, the term of this patent is extended or adjusted under 35 U.S.C. 154(b) by 0 days. days.

(21) Appl. No.: 13/094,783

(22) Filed: Apr. 26, 2011

(65) Prior Publication Data

US 2011/0288546 A1    Nov. 24, 2011

Related U.S. Application Data

(63) Continuation-in-part of application No. 12/472,657, filed on May 27, 2009, now Pat. No. 9,402,679.

(60) Provisional application No. 61/056,207, filed on May 27, 2008, provisional application No. 61/327,792, filed on Apr. 26, 2010.

(51) Int. Cl.
*A61B 18/04* (2006.01)
*A61B 18/08* (2006.01)
*A61B 18/14* (2006.01)
*A61B 18/00* (2006.01)

(52) U.S. Cl.
CPC ........ *A61B 18/085* (2013.01); *A61B 18/1445* (2013.01); *A61B 2018/0063* (2013.01); *A61B 2018/00345* (2013.01); *A61B 2018/00404* (2013.01); *A61B 2018/00601* (2013.01); *A61B 2018/00916* (2013.01)

(58) Field of Classification Search
CPC .................................................. A61B 18/085
USPC ................................ 606/27, 50, 52, 206, 207
See application file for complete search history.

(56) References Cited

U.S. PATENT DOCUMENTS

| | | |
|---|---|---|
| 2,137,710 A | 12/1937 | Anderson |
| 4,031,898 A | 6/1977 | Hiltebrandt et al. |
| 4,071,028 A | 1/1978 | Perkins |
| 4,128,099 A | 12/1978 | Bauer |
| 4,281,646 A | 8/1981 | Kinoshita |
| 4,418,692 A | 12/1983 | Guay |
| 4,468,217 A | 8/1984 | Kuzmick et al. |
| 4,759,362 A | 7/1988 | Taniguchi |
| 4,767,519 A | 8/1988 | de Nora |
| 4,801,015 A | 1/1989 | Lubock et al. |

(Continued)

FOREIGN PATENT DOCUMENTS

| | | |
|---|---|---|
| AU | 2006229913 B2 | 11/2011 |
| CA | 2602015 A1 | 10/2006 |

(Continued)

OTHER PUBLICATIONS

International Search Report and Written Opinion dated Jan. 19, 2010 for PCT Application No. PCT/ US2009/045272.

(Continued)

*Primary Examiner* — Thomas Giuliani
(74) *Attorney, Agent, or Firm* — Kirk Swenson; Wesley Scott Ashton

(57) ABSTRACT

A surgical instrument includes a jaw assembly having a first jaw that includes a support structure with an opening, an electrically insulative material disposed on the support structure, and an operative element for applying energy to tissue, wherein the electrically insulative material extends through the opening of the support structure to thereby secure the electrically insulative material to the support structure.

23 Claims, 15 Drawing Sheets

(56) References Cited

U.S. PATENT DOCUMENTS

| | | | |
|---|---|---|---|
| 4,884,559 A | 12/1989 | Collins |
| 5,009,661 A | 4/1991 | Michelson |
| 5,052,402 A | 10/1991 | Bencini et al. |
| 5,098,430 A | 3/1992 | Fleenor |
| 5,108,474 A | 4/1992 | Riedy et al. |
| 5,147,356 A | 9/1992 | Bhatta |
| 5,151,102 A | 9/1992 | Kamiyama et al. |
| 5,154,709 A | 10/1992 | Johnson |
| 5,156,613 A | 10/1992 | Sawyer |
| 5,160,334 A | 11/1992 | Billings et al. |
| 5,217,460 A | 6/1993 | Knoepfler |
| 5,258,006 A | 11/1993 | Rydell et al. |
| 5,282,799 A | 2/1994 | Rydell |
| 5,290,278 A | 3/1994 | Anderson |
| 5,300,065 A | 4/1994 | Anderson |
| 5,312,426 A | 5/1994 | Segawa et al. |
| 5,314,424 A | 5/1994 | Nicholas |
| 5,318,040 A | 6/1994 | Kensey et al. |
| 5,336,221 A | 8/1994 | Anderson |
| 5,342,381 A | 8/1994 | Tidemand |
| 5,352,222 A | 10/1994 | Rydell |
| 5,356,408 A | 10/1994 | Rydell |
| 5,361,583 A | 11/1994 | Huitema |
| 5,364,395 A | 11/1994 | West, Jr. |
| 5,383,888 A | 1/1995 | Zvenyatsky et al. |
| 5,405,344 A | 4/1995 | Williamson et al. |
| 5,443,463 A | 8/1995 | Stern et al. |
| 5,445,638 A | 8/1995 | Rydell |
| 5,451,222 A | 9/1995 | De Maagd et al. |
| 5,453,599 A | 9/1995 | Hall, Jr. |
| 5,462,546 A | 10/1995 | Rydell |
| 5,472,442 A | 12/1995 | Klicek |
| 5,496,317 A | 3/1996 | Goble et al. |
| 5,507,744 A | 4/1996 | Tay et al. |
| 5,507,773 A | 4/1996 | Huitema et al. |
| 5,509,922 A | 4/1996 | Aranyi et al. |
| 5,514,134 A | 5/1996 | Rydell et al. |
| 5,562,503 A | 10/1996 | Eliman et al. |
| 5,599,350 A | 2/1997 | Schulze et al. |
| 5,624,452 A | 4/1997 | Yates |
| 5,647,871 A | 7/1997 | Levine et al. |
| 5,669,934 A | 9/1997 | Sawyer |
| 5,674,219 A | 10/1997 | Monson et al. |
| 5,683,412 A | 11/1997 | Scarfone |
| 5,709,675 A | 1/1998 | Williams |
| 5,709,680 A | 1/1998 | Yates et al. |
| 5,716,366 A | 2/1998 | Yates |
| 5,722,962 A | 3/1998 | Garcia |
| 5,741,285 A | 4/1998 | McBrayer et al. |
| 5,752,973 A | 5/1998 | Kieturakis |
| 5,755,717 A * | 5/1998 | Yates ................ A61B 18/1482 606/41 |
| 5,766,134 A | 6/1998 | Lisak et al. |
| 5,766,166 A | 6/1998 | Hooven |
| 5,776,130 A | 7/1998 | Buysse et al. |
| 5,807,393 A | 9/1998 | Williamson et al. |
| 5,810,810 A | 9/1998 | Tay et al. |
| 5,810,811 A | 9/1998 | Yates et al. |
| 5,827,271 A | 10/1998 | Buysse et al. |
| 5,833,690 A | 11/1998 | Yates et al. |
| 5,843,017 A | 12/1998 | Yoon |
| 5,849,011 A | 12/1998 | Jones et al. |
| 5,853,410 A | 12/1998 | Greff et al. |
| 5,860,975 A | 1/1999 | Goble et al. |
| 5,871,496 A | 2/1999 | Ginn et al. |
| 5,891,141 A | 4/1999 | Rydell |
| 5,906,630 A | 5/1999 | Anderhub et al. |
| 5,908,420 A | 6/1999 | Parins et al. |
| 5,911,719 A | 6/1999 | Eggers |
| 5,944,718 A | 8/1999 | Austin et al. |
| 5,947,984 A | 9/1999 | Whipple |
| 5,954,686 A | 9/1999 | Garito et al. |
| 5,997,533 A | 12/1999 | Kuhns |
| 6,004,320 A | 12/1999 | Casscells et al. |
| 6,022,313 A | 2/2000 | Ginn et al. |
| 6,024,741 A | 2/2000 | Williamson et al. |
| 6,027,501 A | 2/2000 | Goble et al. |
| 6,033,424 A | 3/2000 | Ouchi |
| 6,039,733 A | 3/2000 | Buysse et al. |
| 6,059,781 A | 5/2000 | Yamanashi et al. |
| 6,066,151 A | 5/2000 | Miyawaki et al. |
| 6,074,389 A | 6/2000 | Levine et al. |
| 6,110,190 A | 8/2000 | Ginn et al. |
| 6,113,596 A | 9/2000 | Hooven et al. |
| 6,174,309 B1 | 1/2001 | Wrublewski et al. |
| 6,190,386 B1 | 2/2001 | Rydell |
| 6,206,876 B1 | 3/2001 | Levine et al. |
| 6,254,623 B1 | 7/2001 | Haibel et al. |
| 6,267,761 B1 | 7/2001 | Ryan |
| 6,270,497 B1 | 8/2001 | Sekino et al. |
| 6,273,887 B1 | 8/2001 | Yamauchi et al. |
| 6,352,503 B1 | 3/2002 | Matsui et al. |
| 6,352,532 B1 | 3/2002 | Kramer et al. |
| 6,391,029 B1 | 5/2002 | Hooven et al. |
| 6,406,454 B1 | 6/2002 | Hajianpour |
| 6,432,105 B1 | 8/2002 | Ellman et al. |
| 6,458,122 B1 | 10/2002 | Pozzato |
| 6,464,701 B1 | 10/2002 | Hooven et al. |
| 6,478,794 B1 | 11/2002 | Trapp et al. |
| 6,517,536 B2 | 2/2003 | Hooven et al. |
| 6,524,307 B1 | 2/2003 | Palmerton et al. |
| 6,527,771 B1 | 3/2003 | Weadock et al. |
| 6,544,210 B1 | 4/2003 | Trudel et al. |
| 6,551,313 B1 | 4/2003 | Levin |
| 6,576,033 B1 | 6/2003 | Booth |
| 6,582,451 B1 | 6/2003 | Marucci et al. |
| 6,582,582 B2 | 6/2003 | Becking |
| 6,602,252 B2 | 8/2003 | Mollenauer |
| 6,613,069 B2 | 9/2003 | Boyd et al. |
| 6,626,901 B1 | 9/2003 | Treat et al. |
| 6,652,514 B2 | 11/2003 | Eliman et al. |
| 6,656,177 B2 | 12/2003 | Truckai et al. |
| 6,663,610 B1 | 12/2003 | Thompson et al. |
| 6,682,528 B2 | 1/2004 | Frazier et al. |
| 6,685,665 B2 | 2/2004 | Booth et al. |
| 6,695,837 B2 | 2/2004 | Howell |
| 6,746,504 B2 | 6/2004 | Booth |
| 6,770,072 B1 | 8/2004 | Truckai et al. |
| 6,773,409 B2 | 8/2004 | Truckai et al. |
| 6,802,843 B2 | 10/2004 | Truckai et al. |
| 6,821,273 B2 | 11/2004 | Mollenauer |
| 6,830,569 B2 | 12/2004 | Thompson et al. |
| 6,860,880 B2 | 3/2005 | Treat et al. |
| 6,908,463 B2 | 6/2005 | Treat et al. |
| 6,958,070 B2 | 10/2005 | Witt et al. |
| 6,966,907 B2 | 11/2005 | Goble |
| 6,966,909 B2 | 11/2005 | Marshall et al. |
| 6,994,707 B2 | 2/2006 | Ellman et al. |
| 7,033,356 B2 | 4/2006 | Latterell et al. |
| 7,083,620 B2 | 8/2006 | Jahns et al. |
| 7,094,231 B1 | 8/2006 | Eliman et al. |
| 7,112,199 B2 | 9/2006 | Cosmescu |
| 7,147,637 B2 | 12/2006 | Goble |
| 7,204,835 B2 | 4/2007 | Latterell et al. |
| 7,211,080 B2 | 5/2007 | Treat et al. |
| 7,306,599 B2 | 12/2007 | Karasawa et al. |
| 7,316,683 B2 | 1/2008 | Kasahara et al. |
| 7,326,202 B2 | 2/2008 | McGaffigan |
| 7,329,257 B2 * | 2/2008 | Kanehira et al. ............... 606/52 |
| 7,364,577 B2 | 4/2008 | Wham et al. |
| 7,367,976 B2 | 5/2008 | Lawes et al. |
| 7,396,356 B2 | 7/2008 | Mollenauer |
| 7,513,896 B2 | 4/2009 | Orszulak |
| 7,632,270 B2 | 12/2009 | Livneh |
| 7,645,289 B2 | 1/2010 | Bayer |
| 7,695,470 B1 | 4/2010 | Stewart et al. |
| 7,699,861 B2 | 4/2010 | Bayer |
| 7,887,558 B2 | 2/2011 | Lin et al. |
| 7,918,845 B2 | 4/2011 | Saadat et al. |
| 7,918,848 B2 | 4/2011 | Lau et al. |
| 8,197,472 B2 | 6/2012 | Lau et al. |
| 8,221,306 B2 | 7/2012 | Okada et al. |
| 8,251,989 B1 | 8/2012 | Newton et al. |
| 8,257,352 B2 | 9/2012 | Lawes et al. |

(56) References Cited

U.S. PATENT DOCUMENTS

| | | |
|---|---|---|
| 8,425,508 B2 | 4/2013 | Kasahara et al. |
| 8,623,003 B2 | 1/2014 | Lau et al. |
| 8,657,818 B2 | 2/2014 | Lin |
| 8,894,638 B2 | 11/2014 | Lau et al. |
| 8,961,503 B2 | 2/2015 | Lau et al. |
| 9,402,680 B2 | 8/2016 | Ginnebaugh et al. |
| 2002/0019631 A1 | 2/2002 | Kidder et al. |
| 2002/0058938 A1 | 5/2002 | Cosmescu |
| 2002/0115997 A1 | 8/2002 | Truckai et al. |
| 2002/0128603 A1 | 9/2002 | Booth et al. |
| 2003/0014052 A1 | 1/2003 | Buysse et al. |
| 2003/0060816 A1 | 3/2003 | Iida |
| 2003/0073991 A1* | 4/2003 | Francischelli ............... 606/41 |
| 2003/0073994 A1 | 4/2003 | Schulze |
| 2003/0125734 A1 | 7/2003 | Mollenauer |
| 2003/0130654 A1 | 7/2003 | Kasahara et al. |
| 2003/0130674 A1 | 7/2003 | Kasahara et al. |
| 2003/0130675 A1 | 7/2003 | Kasahara et al. |
| 2003/0139649 A1 | 7/2003 | Kasahara et al. |
| 2003/0144652 A1 | 7/2003 | Baker et al. |
| 2003/0144660 A1 | 7/2003 | Mollenauer |
| 2003/0163123 A1 | 8/2003 | Goble et al. |
| 2003/0171747 A1 | 9/2003 | Kanehira et al. |
| 2003/0187429 A1 | 10/2003 | Karasawa et al. |
| 2004/0054365 A1 | 3/2004 | Goble |
| 2004/0064151 A1 | 4/2004 | Mollenauer |
| 2004/0078035 A1 | 4/2004 | Kanehira et al. |
| 2004/0102450 A1 | 5/2004 | Ewing et al. |
| 2004/0133228 A1 | 7/2004 | Bayer |
| 2004/0176756 A1 | 9/2004 | McGaffigan |
| 2004/0204725 A1 | 10/2004 | Bayer |
| 2004/0260279 A1 | 12/2004 | Goble et al. |
| 2005/0033278 A1 | 2/2005 | McClurken et al. |
| 2005/0049633 A1 | 3/2005 | Watanabe |
| 2005/0072827 A1 | 4/2005 | Mollenauer |
| 2005/0113826 A1* | 5/2005 | Johnson ............ A61B 18/1442 606/45 |
| 2005/0113828 A1 | 5/2005 | Shields et al. |
| 2005/0171533 A1 | 8/2005 | Latterell et al. |
| 2006/0041254 A1 | 2/2006 | Francischelli et al. |
| 2006/0074444 A1 | 4/2006 | Lin et al. |
| 2006/0211916 A1 | 9/2006 | Kasahara et al. |
| 2006/0217697 A1 | 9/2006 | Lau et al. |
| 2006/0217706 A1* | 9/2006 | Lau .................. A61B 17/29 606/45 |
| 2006/0235379 A1* | 10/2006 | McClurken et al. ......... 606/45 |
| 2006/0271037 A1* | 11/2006 | Maroney ........... A61B 18/1442 606/45 |
| 2007/0021405 A1 | 1/2007 | Abouabdellah et al. |
| 2007/0021424 A1 | 1/2007 | Abouabdellah et al. |
| 2007/0027141 A1 | 2/2007 | Abouabdellah et al. |
| 2007/0078456 A1 | 4/2007 | Dumbauld et al. |
| 2007/0149993 A1 | 6/2007 | Kasahara et al. |
| 2007/0173814 A1 | 7/2007 | Hixson et al. |
| 2007/0213749 A1 | 9/2007 | Kogasaka et al. |
| 2007/0260242 A1 | 11/2007 | Dycus et al. |
| 2007/0293856 A1 | 12/2007 | Paul et al. |
| 2007/0293858 A1 | 12/2007 | Fischer |
| 2008/0015567 A1* | 1/2008 | Kimura ........................ 606/41 |
| 2008/0015575 A1* | 1/2008 | Odom et al. ................. 606/51 |
| 2008/0039835 A1 | 2/2008 | Johnson et al. |
| 2008/0154091 A1 | 6/2008 | Dejima et al. |
| 2008/0306335 A1 | 12/2008 | Lau et al. |
| 2009/0024121 A1 | 1/2009 | Kasahara et al. |
| 2009/0118730 A1 | 5/2009 | Mollenauer |
| 2009/0299367 A1 | 12/2009 | Ginnebaugh et al. |
| 2010/0048992 A1 | 2/2010 | Okada et al. |
| 2010/0292533 A1 | 11/2010 | Kasahara et al. |
| 2011/0046439 A1 | 2/2011 | Pamnani et al. |
| 2011/0046624 A1 | 2/2011 | Lin |
| 2011/0257643 A1 | 10/2011 | Lau et al. |
| 2011/0288369 A1 | 11/2011 | Ginnebaugh et al. |
| 2011/0288546 A1 | 11/2011 | Abbott et al. |
| 2012/0283720 A1 | 11/2012 | Newton et al. |
| 2012/0316550 A1 | 12/2012 | Ullrich, Jr. et al. |
| 2013/0018373 A1 | 1/2013 | Lau et al. |
| 2014/0194876 A1 | 7/2014 | Lau et al. |

FOREIGN PATENT DOCUMENTS

| | | |
|---|---|---|
| CA | 2602381 A1 | 10/2006 |
| DE | 10328514 B3 | 3/2005 |
| EP | 538984 A2 | 4/1993 |
| EP | 538984 A3 | 7/1993 |
| EP | 538984 B1 | 3/1997 |
| EP | 1330991 | 7/2003 |
| EP | 1632192 | 3/2006 |
| EP | 1330991 B1 | 9/2007 |
| EP | 1878399 | 1/2008 |
| EP | 1894535 | 3/2008 |
| EP | 1632192 B1 | 3/2009 |
| EP | 2106762 A1 | 10/2009 |
| EP | 1885270 B1 | 8/2010 |
| EP | 1861034 B1 | 9/2010 |
| EP | 2285305 A2 | 2/2011 |
| EP | 1894535 A3 | 3/2011 |
| JP | H0750866 A | 9/1995 |
| JP | H10511030 A | 10/1998 |
| JP | 2000135222 A | 5/2000 |
| JP | 2000139943 A | 5/2000 |
| JP | 2003144451 A | 5/2003 |
| JP | 2005058553 A | 3/2005 |
| JP | 2005514102 A | 5/2005 |
| JP | 2008534068 A | 8/2008 |
| JP | 2008534069 A | 8/2008 |
| JP | 2011521723 A | 7/2011 |
| JP | 4966959 B2 | 7/2012 |
| WO | 1993020769 A1 | 10/1993 |
| WO | 1997005829 A1 | 2/1997 |
| WO | 1997010764 A1 | 3/1997 |
| WO | 2000047124 A1 | 8/2000 |
| WO | 2002080794 A1 | 10/2002 |
| WO | 2003057058 A1 | 7/2003 |
| WO | 2003061456 A2 | 7/2003 |
| WO | 2003061456 A3 | 1/2004 |
| WO | WO 2005048863 | 6/2005 |
| WO | 2006104835 A1 | 10/2006 |
| WO | 2006104836 A2 | 10/2006 |
| WO | 2006104836 A3 | 1/2007 |
| WO | WO 2009039179 | 3/2009 |
| WO | 2009154976 A2 | 12/2009 |
| WO | 2009154976 A3 | 3/2010 |
| WO | 2009154976 A4 | 5/2010 |
| WO | 2009154976 A9 | 2/2011 |

OTHER PUBLICATIONS

Non-Final Office Action dated May 7, 2012 for U.S. Appl. No. 12/472,657.

Stedman's Medical Dictionary, pp. 3 and 238 (1982), Waverly Press, Inc.

U.S. Appl. No. 13/494,985, filed Jun. 12, 2012.

U.S. Appl. 13/549,367, filed Jul. 13, 2012.

U.S. Appl. No. 12/545,690, filed Aug. 21, 2009.

PCT International Search Report and Written Opinion, PCT/US2006/010569, dated Jul. 24, 2006, 20 pages.

PCT International Preliminary Report on Patentability, PCT/US2006/010569, dated Sep. 25, 2007, 9 pages.

PCT International Search Report and Written Opinion, PCT/US2006/010568, dated Jul. 24, 2006, 8 pages.

PCT International Preliminary Report on Patentability, PCT/US2006/010568, dated Sep. 25, 2007, 6 pages.

European Examination Report, EP 06739388.4, dated Sep. 17, 2008, 7 pages.

English translation of the abstract for JP Publication No. 2003-144451 dated May 20, 2003.

English translation of the abstract for JP Application No. 2003-294157 (Publication No. 2005-058553) dated Mar. 10, 2005.

European Examination Report, EP Application No. EP 06739387.6, dated Dec. 11, 2008 (4 pages).

(56) References Cited

OTHER PUBLICATIONS

U.S. Appl. No. 13/047,778, filed Mar. 14, 2011.
U.S. Appl. No. 14/148,671, filed Jan. 6, 2014,
U.S. Appl. No. 12/472,657, filed May 27, 2009.
L.S. Feldman et al. (eds.), Fundamentals of Electrosurgery Part I: Principles of Radiofrequency Energy for Surgery, the SAGES Manual on the Fundamental Use of Surgical Energy (FUSE), 2012, 15-59, Springer-Verlag, New York.
Dielectric Heating, downloaded Dec. 2, 2014 from http://www.comdel.com/dielectric-heating, 2 pages.
Ghanian, Hans C., Physics, 1985, 658-660, W.W. Norton & Company, Inc., New York.
How RF Heating Works, downloaded Dec. 2, 2014 from http://www.macrowave.com/rftech.html, 1 page.
Electrosurgery: the newest energy-based devices downloaded Dec. 3, 2014 from http://contemporary.obgyn.modernmedicine.com/contemporary-obgyn/content/tags/aescula . . . , 6 pages.
Stedman's Medical Dictionary, 1982, 3 and 238, $24^{th}$ ed., Williams & Wilkins, Baltimore, MD, US.
Joule heating, Wikipedia, downloaded Dec. 1, 2014 from http://en.wikipedia.org/wiki/Joule_heating, 6 pages.

* cited by examiner

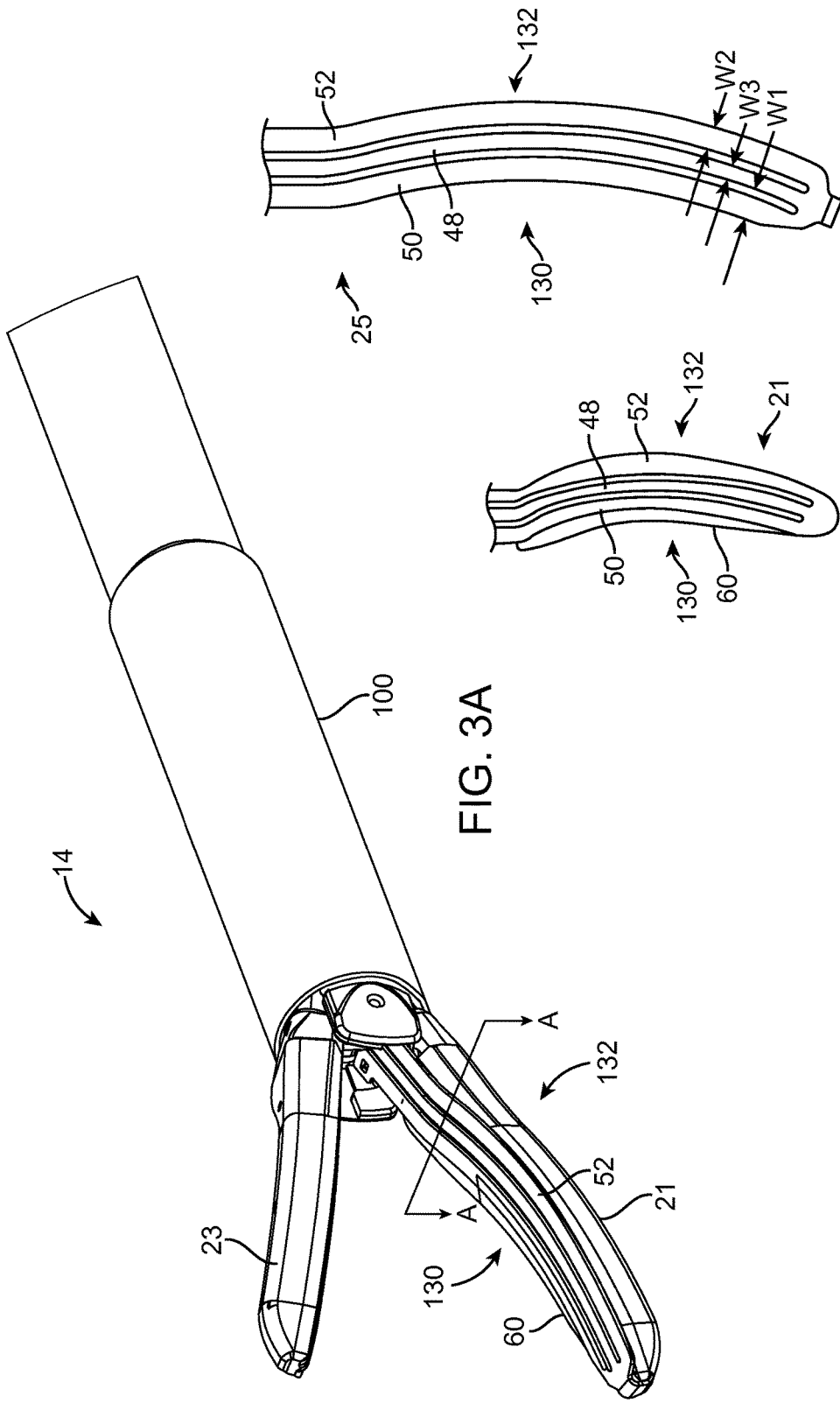

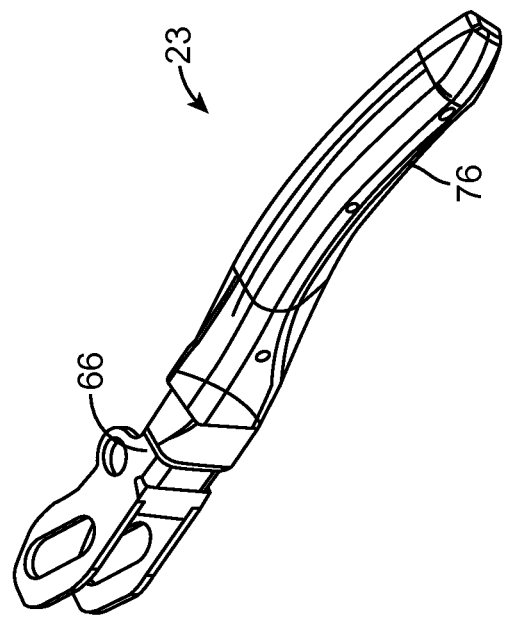
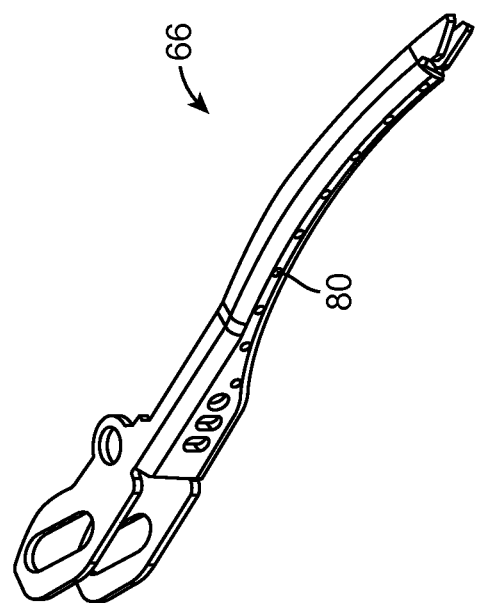

SURGICAL INSTRUMENT AND METHOD

RELATED APPLICATION DATA

This application is a continuation-in-part of U.S. patent application Ser. No. 12/472,657, filed on May 27, 2009, now U.S. Pat. No. 9,402,679, which claims priority to U.S. provisional patent application Ser. No. 61/056,207, filed on May 27, 2008, and also claims priority to and the benefit of U.S. provisional patent application Ser. No. 61/327,792, filed Apr. 26, 2010, the entire disclosures of all of which are expressly incorporated by reference herein.

FIELD

This application relates to a surgical instrument, and more particularly, to a surgical instrument for use in a vessel harvesting procedure.

BACKGROUND

In endoscopic vessel harvesting (EVH) surgical procedures, a long slender surgical instrument may be introduced into a tunnel next to a target vessel (e.g., a saphenous vein or a radial artery) in a patient, and advanced along the vessel to dissect the vessel away from adjacent tissue and to sever side-branch vessels along the course of the target vessel.

EVH devices for performing vessel harvesting may include a jaw assembly with a heating element. During use, the jaw assembly is used to grasp a vessel or tissue, and the heating element is activated to cut and seal the vessel or tissue. Sometimes, during use of such an EVH device, the heating element may be activated for too long of a duration, thereby causing the device to overheat. Also, the jaw assembly may be closed and the heating element activated without grasping tissue between the jaws. This may cause the jaw assembly to overheat more quickly because of the absence of tissue between the jaws to absorb the thermal energy from the heating element. The resulting high temperature may cause material and mechanism failures, such as degradation of jaw members, melting of mechanical linkages, destruction of electrical circuit, etc.

Also, existing EVH devices do not have any mechanism for controlling the delivery of energy to tissue in a manner that ensures that tissue is transected quickly while simultaneously preventing overheating of the tissue.

SUMMARY

In accordance with some embodiments, a surgical instrument includes a jaw assembly having a first jaw that includes a support structure with an opening, an electrically insulative material disposed on the support structure, and an operative element for applying energy to tissue, wherein the electrically insulative material extends through the opening of the support structure to thereby secure the electrically insulative material to the support structure.

In accordance with other embodiments, a surgical instrument includes a jaw assembly for grasping tissue, the jaw assembly having an operative element, a user control for controlling a delivery of energy to the operative element, and a device configured to prevent a delivery of energy, or reduce an amount of energy being delivered, to the operative element under a predetermined condition after the operative element has been activated, thereby overriding the user control under the predetermined condition.

In accordance with other embodiments, a surgical instrument includes a jaw assembly having a first jaw and a second jaw, the first and second jaws movable between an open state and a closed state in which at least a portion of the first and second jaws are closer to each other, wherein a proximal portion of the jaw assembly defines a barrier that inhibits tissue located between the first and second jaws from moving proximally past the barrier when the jaws are in the open state, and an operative element for applying energy to tissue, wherein the operative element is located at the jaw assembly, wherein the operative element extends along the jaw assembly from the barrier to a location that is distal of the barrier.

In accordance with other embodiments, a surgical kit includes a cannula having a lumen, and an instrument sized for insertion into the lumen of the cannula, the instrument having a jaw assembly configured for grasping tissue, the jaw assembly having an operative element, a user control for controlling a delivery of energy to the operative element, and a device configured to prevent a delivery of energy, or reduce an amount of energy being delivered, to the operative element under a predetermined condition after the operative element has been activated, thereby overriding the user control under the predetermined condition.

In accordance with other embodiments, a surgical kit includes a cannula having a lumen, and an instrument sized for insertion into the lumen of the cannula, the instrument having a jaw assembly having a first jaw and a second jaw, the first and second jaws movable between an open state and a closed state in which at least a portion of the first and second jaws are closer to each other, wherein a proximal portion of the jaw assembly defines a barrier that inhibits tissue located between the first and second jaws from moving proximally past the barrier when the jaws are in the open state, and an operative element for applying energy to tissue, wherein the operative element is located at the jaw assembly, wherein the operative element extends from the barrier to a location that is distal of the barrier.

In accordance with other embodiments, a surgical method includes holding tissue between two jaws of a jaw assembly, delivering energy to an operative element at the jaw assembly in response to an operation of a control by a user, and overriding the operation of the control by preventing a delivery of energy, or reducing an amount of energy being delivered, to the operative element when a predetermined condition has occurred.

In accordance with other embodiments, a surgical instrument includes a jaw assembly having a first jaw that includes a support structure with an opening, an electrically insulative material disposed on the support structure, and an operative element for applying energy to tissue, wherein the operative element has a first outer portion and a second outer portion configured to seal tissue, and an inner portion configured to sever tissue, each of the first outer portion and the second outer portion is crescent shaped, and an outer edge of the second outer portion that is on a convex side of the first jaw extends from the insulative material for at least a lengthwise portion of the first jaw.

In accordance with some embodiments, a surgical instrument for use in a vessel harvesting procedure includes a jaw assembly having a first jaw that includes a support structure with an opening, an electrically insulative material disposed on the support structure, and an operative element for applying energy to tissue, wherein the electrically insulative material extends through the opening of the support structure to thereby secure the electrically insulative material to the support structure.

In accordance with other embodiments, the jaw assembly has a protrusion for abutment against a main vessel, and the protrusion is sized so that when the protrusion is abutted against the main vessel, the operative element is automatically placed at a desired position relative to a side branch vessel.

In accordance with other embodiments, the electrically insulative material is overmolded onto the support structure and through the opening of the support structure.

In accordance with other embodiments, the electrically insulative material is mechanically coupled to the support structure without using an adhesive.

In accordance with other embodiments, the surgical instrument further includes a sensor mechanically or electrically coupled to the jaw assembly, wherein the sensor is configured to measure a variable related to a temperature at or near the jaw assembly.

In accordance with other embodiments, the surgical instrument further includes a regulator configured to control a delivery of energy to the jaw assembly based at least in part on the measured variable.

In accordance with other embodiments, the surgical instrument further includes a regulator configured to control a delivery of energy to the jaw assembly such that a temperature at or near the jaw assembly stays below a predetermined limit.

In accordance with other embodiments, the surgical instrument further includes a regulator for preventing a delivery of energy to the jaw assembly for a predetermined duration after the operative element has been energized.

In accordance with other embodiments, the predetermined duration is variable as a function of a duration for which the operative element has been energized, a temperature at or near the jaw assembly, or a variable that corresponds with the temperature at or near the jaw assembly.

In accordance with other embodiments, the operative element comprises an electrode secured to the first jaw.

In accordance with other embodiments, the electrode has an edge that protrudes from a side of the first jaw.

In accordance with other embodiments, the jaw assembly includes a second jaw, the second jaw having a raised portion that faces towards the first jaw.

In accordance with other embodiments, the second jaw has a raised portion that faces towards the first jaw, and the electrode has two outer electrode portions and an inner electrode portion that is between the two outer electrode portions, the raised portion of the second jaw being in alignment with the inner electrode portion.

In accordance with other embodiments, the surgical instrument further includes a PTC device coupled to the operative element.

In accordance with other embodiments, the surgical instrument further includes a NTC device coupled to the operative element.

In accordance with some embodiments, a surgical instrument for use in a vessel harvesting procedure includes a jaw assembly configured to grasp tissue, the jaw assembly having an operative element, a user control configured to control a delivery of energy to the operative element, and an override device configured under one or more predetermined conditions to override the user control and prevent the delivery of the energy, or reduce an amount of the energy delivered, to the operative element.

In accordance with other embodiments, the override is implemented as a part of the operative element.

In accordance with other embodiments, wherein the override device is configured to prevent or slow down the delivery of the energy to the operative element after the operative element has been activated for a predetermined period or after the operative element has reached a predetermined temperature.

In accordance with other embodiments, the override device is configured to prevent the delivery of the energy to the operative element for a predetermined duration.

In accordance with other embodiments, the predetermined duration is variable.

In accordance with other embodiments, wherein the predetermined duration is a function of a temperature of the override device or of the operative element, a function of an amount of time for which the operative element has been activated, or a function of an actual cool off period undergone by the device or the operative element.

In accordance with other embodiments, wherein the override device comprises a PTC device configured to allow a current to be delivered to the operative element, and prevent a delivery of the current to the operative element in response to a temperature rise.

In accordance with other embodiments, the override device comprises a NTC device configured to provide an electrical resistance, and reduce the electrical resistance in response to a temperature rise.

In accordance with other embodiments, the override device or the operative element is configured to increase its resistance to a predetermined resistance value in response to the device or the operative element reaching a predetermined temperature.

In accordance with other embodiments, when the override device or the operative element reaches the predetermined resistance value, the operative element does not substantially deliver additional energy.

In accordance with other embodiments, wherein when the override device or the operative element reaches the predetermined resistance value, the operative element delivers additional energy in a predetermined manner.

In accordance with some embodiments, a surgical instrument for use in a vessel harvesting procedure includes a jaw assembly having a first jaw and a second jaw, the first and second jaws movable between an open state and a closed state in which at least a portion of the first and second jaws are closer to each other, wherein the jaw assembly further includes a barrier that is distal to a proximal end of the first jaw, the barrier configured to inhibit tissue located between the first and second jaws from moving proximally past the barrier when the jaws are in the open state, and an operative element for applying energy to tissue, wherein the operative element is located at the jaw assembly, wherein the operative element extends along the jaw assembly from the barrier to a location that is distal of the barrier.

In accordance with other embodiments, the operative element extends along the jaw assembly from a location proximal of the barrier to the location that is distal of the barrier.

In accordance with other embodiments, the operative element includes an electrode.

In accordance with other embodiments, the electrode includes a first portion configured to weld tissue, and a second portion configured to cut tissue.

In accordance with other embodiments, the first portion is coupled to the first jaw, and the second portion is coupled to the second jaw.

In accordance with other embodiments, the first and second portions are coupled to the first jaw.

In accordance with some embodiments, a surgical kit for use in a vessel harvesting procedure includes a cannula having a lumen, and an instrument sized for insertion into the lumen of the cannula, the instrument having a jaw assembly configured to grasp tissue, the jaw assembly having an operative element, a user control configured to control a delivery of energy to the operative element, and an override device configured under one or more predetermined conditions to override the user control and prevent the delivery of the energy, or reduce an amount of the energy delivered, to the operative element.

In accordance with some embodiments, a surgical kit for use in a vessel harvesting procedure includes a cannula having a lumen, and an instrument sized for insertion into the lumen of the cannula, the instrument having a jaw assembly having a first jaw and a second jaw, the first and second jaws movable between an open state and a closed state in which at least a portion of the first and second jaws are closer to each other, wherein the jaw assembly further includes a barrier that is distal to a proximal end of the first jaw, the barrier configured to inhibit tissue located between the first and second jaws from moving proximally past the barrier when the jaws are in the open state, and an operative element for applying energy to tissue, wherein the operative element is located at the jaw assembly, wherein the operative element extends from the barrier to a location that is distal of the barrier.

In accordance with some embodiments, a surgical method includes holding tissue between two jaws of a jaw assembly, delivering energy to an operative element at the jaw assembly in response to an operation of a control by a user, and overriding the operation of the control by preventing a delivery of energy, or reducing an amount of energy being delivered, to the operative element when a predetermined condition has occurred.

In accordance with other embodiments, the predetermined condition has occurred when the operative element has reached a predetermined temperature.

In accordance with other embodiments, the predetermined condition has occurred when the operative element has been activated for a predetermined period.

In accordance with other embodiments, the method further includes inhibiting the tissue located between the two jaws from moving proximally past a barrier defined by the jaw assembly.

In accordance with other embodiments, the tissue is abutted against the barrier, and the energy is delivered to the operative element to heat the tissue while the tissue is abutted against the barrier.

In accordance with other embodiments, the tissue comprises vessel tissue.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 3A shows the surgical instrument of FIG. 2, showing that the instrument has an insulative element;

FIG. 3B shows an overhead view of one of the jaws of FIG. 3A as viewed through lines A-A.

FIG. 3C shows an overhead view of an electrode used with the jaw of FIG. 3B.

FIG. 6A illustrates a perspective view of a support structure for another jaw in accordance with some embodiments;

FIG. 6B illustrates a perspective view of a jaw, showing an insulative element integrated into the support structure of FIG. 6A;

DETAILED DESCRIPTION

Figure 1:
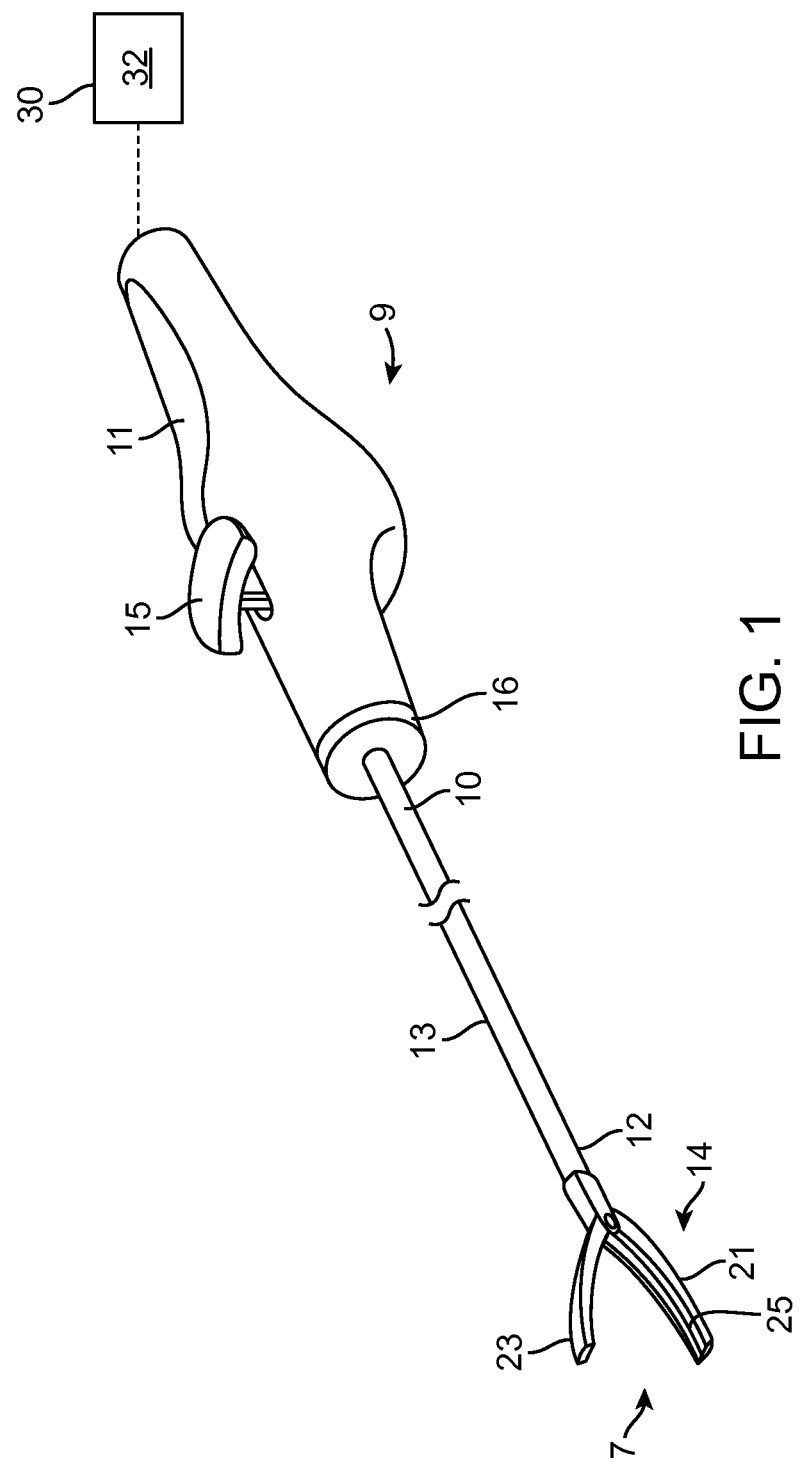
FIG. 1 illustrates a surgical instrument in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a surgical instrument 9 in accordance with some embodiments. The surgical instrument 9 includes a handle 11, an elongated body 13 having a proximal end 10 and a distal end 12, and a surgical device 14 located at the distal end 12 of the body 13. The proximal end 10 of the elongated body 13 is coupled to a distal end 16 of the handle 11. As used in this specification, the term "surgical device" refers to any device or component that may be used to operate on tissue (e.g., to treat, manipulate, handle, hold, cut, heat, seal, cauterize, or energize, etc., tissue). The elongated body 13 may be rigid, or alternatively, flexible. The handle 11 includes an actuator 15 (e.g., a button) that is coupled to the surgical device 14 through a linkage (not shown) within a bore of the body 13 for manually controlling an operation of the surgical device 14. The handle 11 and the actuator 15 are preferably made from insulative material(s) such as plastic.

In the illustrated embodiments, the surgical device 14 is a jaw assembly that includes a pair of jaws 21, 23 for clamping, cutting, and sealing a vessel. The jaw 21 includes an electrically conductive material 25 which faces towards the opposing jaw 23. Alternatively, or additionally, the jaw 23 includes an electrically conductive material which faces towards jaw 21. The electrically conductive material 25 is in a form of an electrode, and is configured to provide heat during use. As used in this specification, the term "electrode" refers to a component that is for delivering energy, such as heat energy, RF energy, etc., and thus, should not be limited to a component that delivers any particular form of energy. Preferably, the electrode is used to deliver heat through joule heating (resistance-based electrosurgical heating). The electrically conductive material 25 may be Ni-chrome, stainless steel, or other metals or alloys in different embodiments. The jaws 21, 23 are configured to close in response to actuation (e.g., pressing, pulling, or pushing, etc.) of the actuator 15, thereby clamping a vessel during use. In the illustrated embodiments, the actuator 15 may be further actuated (e.g., further pressed, further pulled, or further pushed, etc.) to cause the electrically conductive material 25 to provide (e.g., emit) heat, thereby cutting, sealing, or and cutting and sealing the clamped vessel. In particular, when the actuator 15 is further actuated, the electrically conductive material 25 is electrically coupled to a DC source 30, which provides a current to the electrically conductive material (electrode) 25, thereby heating the electrode 25. After the vessel is cut and/or sealed, the actuator 15 may be de-actuated to stop the delivery of current to the electrode 25, and may be further de-actuated to open the jaws 21, 23. The mechanical linkage for translating operation of the actuator 15 into closing and opening of the jaws 21, 23 may be implemented using cables, shafts, gears, or any of other mechanical devices that are known in the art. In other embodiments, the energy source 30 may provide another type of energy, and does not need to be a DC source.

The linkage that mechanically couples the jaws 21, 23 to the actuator 15 may be electrically insulated, for example, by silicone rubber, ceramic or other suitable non-electrically conductive material. In some embodiments, energy is supplied from the energy source 30 via an electric line housed by the body 13 to the electrically conductive material (electrode) 25 at jaw 21 (and/or to the electrode at jaw 23). In other embodiments, the body 13 may not include an electric line for delivering energy to the electrode 25. Instead, the linkage that mechanically couples the jaws 21, 23 to the actuator 15 may be electrically conductive, and is used to deliver energy to the electrode 25 at jaw 21 (and/or to the electrode at jaw 23).

Figure 2:
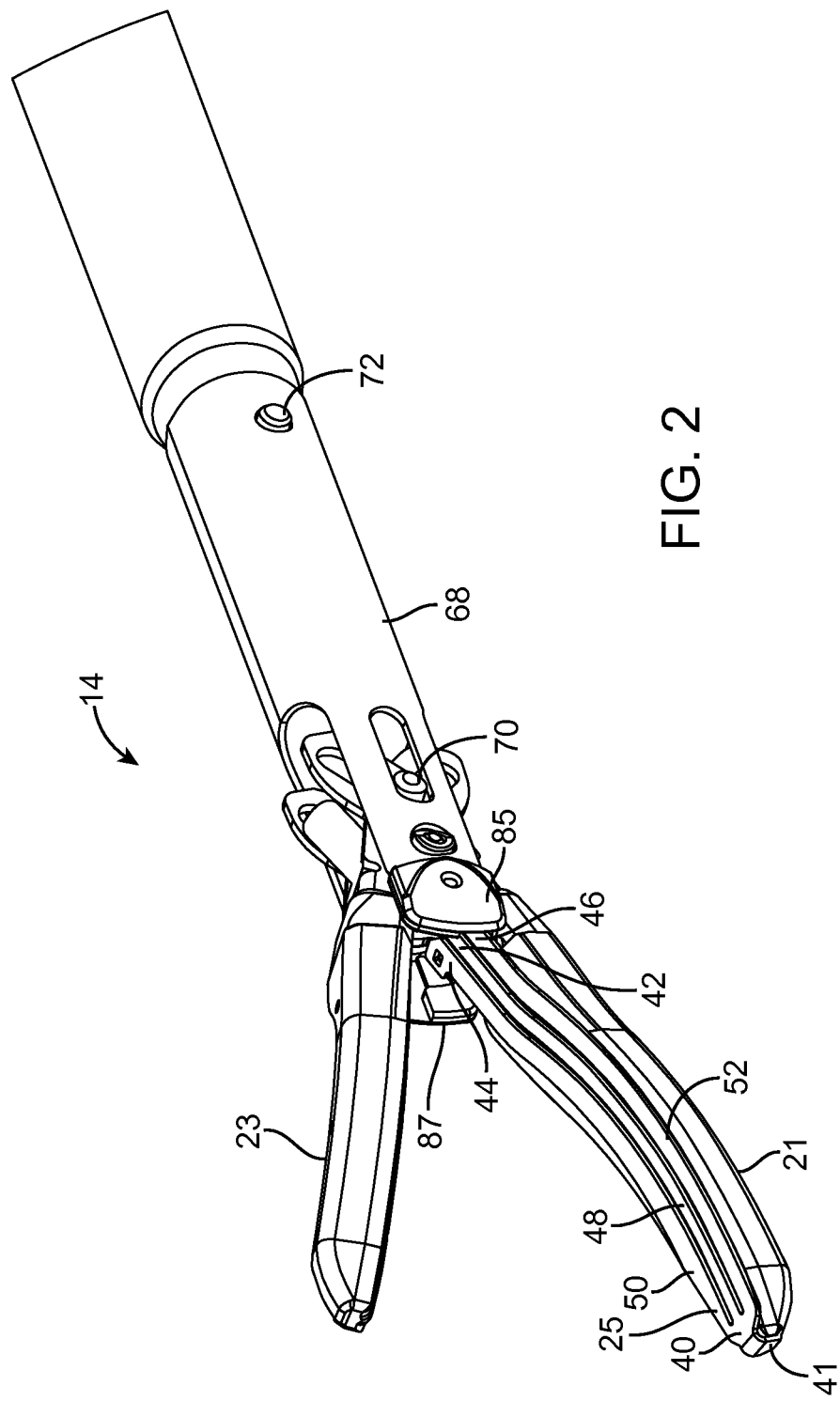
FIG. 2 is a partial perspective view of the distal portion of a surgical instrument depicting a pair of jaws in accordance with some embodiments.

FIG. 2 illustrates the pair of jaws 21, 23 in accordance with some embodiments. As shown in the figure, the electrically conductive material 25 forms a heating element (electrode) 40 that is disposed on a surface of the jaw 21. The heating element 40 includes two (or more) outer portions 50, 52, and an inner (middle) portion 48. In an embodiment of the disclosure, the inner and outer portions conductively and/or structurally meet or extend from a distal end 41. The outer portions 50, 52 have respective outer terminals 44, 46 at their ends (proximal to distal end 41), and the middle portion 48 has an inner terminal 42 at its end. Thus, the portions 48, 50, 52 form an electrical heater circuit between the inner terminal 42 and outer terminals 44, 46. In the illustrated embodiments, the outer portions 50, 52 and the inner portion 48 function as an electrode that is configured to deliver heat during operation, such as through joule heating. In particular, during operation, the inner terminal 42 of the electrode 40 is electrically coupled to a first terminal of the DC source 30, and outer terminals 44, 46 of the electrode 40 are electrically coupled to a second terminal of the DC source 30, thereby allowing the electrode 40 to receive DC energy (e.g., for cutting and/or welding tissue). The heating element 40 may be formed using a single, flat sheet of electrically conductive material (e.g., Ni-chrome alloy, stainless steel, nickel alloys, etc.). Such a structure provides a robust and reliable electrode, and further provides manufacturing and cost advantages. It also reduces the likelihood of tissue build up and entrapment during use by minimizing crevices into which tissue can migrate.

As shown in FIG. 2, the jaw-operating mechanism and linkage thereof may be supported in a metal housing 68 that includes metal sliding pin 70 and attachment pin 72, all covered with an insulating layer 100 (FIG. 3A) of flexible material such as silicone rubber, or the like, to shield/protect adjacent tissue from moving parts and from electrical energy within the instrument. Also, such an insulating cover retains the sliding and attachment pins 70, 72 in place to obviate the need for more expensive fasteners and mechanisms.

During use, current from the DC source 30 is conducted through the inner terminal 42, and flows in the inner (middle) portion 48 of the heating element 40 and in parallel through the dual outer portions 50, 52 of the heating element 40 to the outer terminals 44, 46. Thus, for inner and outer portions 48, 50, 52 of equal thicknesses and equal widths, current density in the inner (middle) portion 48 is twice as high as the current density in each of the outer portions 50, 52 in response to an electrical heater signal (e.g., a voltage) applied between inner terminal 42 and the outer terminals 44, 46. Of course, current densities in the inner and outer portions 48, 50, 52 may be altered (for example, by altering the relative widths of the inner and outer portions, by altering resistances through selection of different materials, by altering both the widths and resistances, etc.) to alter the operating temperatures thereof in response to applied electrical heater signals (e.g., voltages). For example, in some embodiments, the above feature could be achieved in a single planar element by "coining" the materials together such that the material compositions are different between the sections, thereby resulting in larger (or smaller) differences in resistance, if desired. In operation, the outer portions 50, 52 may operate at a temperature sufficient to weld a tissue structure (e.g., a blood vessel) grasped between the jaws 21, 23, and the inner (middle) heater portion 48 may operate at a higher temperature sufficient to sever the grasped tissue structure intermediate of the welded segments.

As shown in FIG. 2, the jaw assembly includes clevises 85 and 87 located between proximal ends of the jaws 21, 23. During use, target tissue may be placed between the jaws 21, 23, and may abut (either intentionally or accidentally) against the clevises 85, 87, thereby limiting proximal travel between the jaws. In the illustrated embodiments, the inner heater portion 48 and the outer portions 50, 52 extend along the jaw 21 proximally and past the distal tips of the clevises 85, 87. Such configuration is advantageous in that it allows the portions 48, 50, 52 to deliver energy to treat the tissue even when the tissue abuts against the clevises 85, 87. Thus, the functional/usable length of the jaws is maximized, in contrast to some other commercial devices that do not perform well at the vertex of the jaws.

FIG. 3B shows an overhead view of jaw 21 of FIG. 3A. From this view, electrode or conductive material 25 is shown to conform with a crescent shape of the jaw 21, having a concave side 130 and a convex side 132. The crescent shape also applies to jaw 23 (not shown). The radius of the crescent shape may be between 0.3 inches, and 1.5 inches. Preferably, the radius is between 0.7 inches and 0.6 inches.

FIG. 3C shows the conductive material 25 of FIG. 3B without the remaining portions of jaw 21 exposed. Further illustrated in FIG. 3C, inner heater portion 48 has a width W3, while outer portions 50 and 52 have a width of W1 and W2 respectively. Preferably, the widths W1, W2, W3 have a width of 0.015 to 0.03 inches, more preferably between 0.018 and 0.025 inches, and most preferably 0.02 inches. Preferably, the inner and outer portions 48, 50, and 52 have a generally continuous gap between each of the portions of the conductive material 25 along the crescent shape.

Figure 3D:
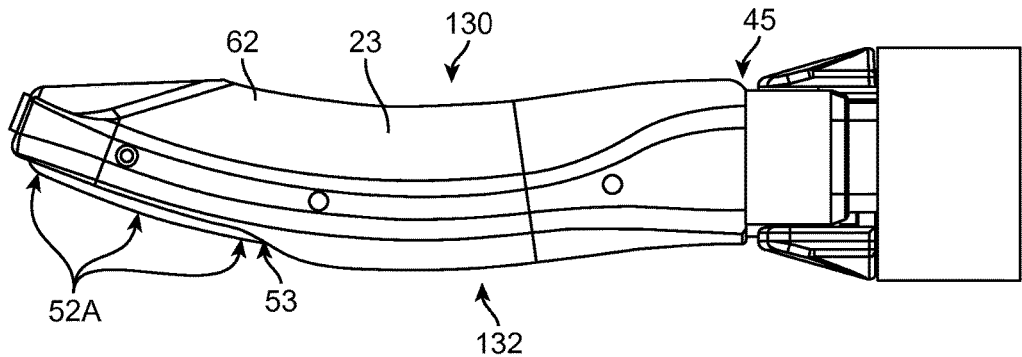
FIG. 3D shows an overhead view of an alternative set of jaws to those of FIG. 3B in accordance with some embodiments.

FIG. 3D shows an overhead view of an alternative embodiment of jaws 23 and 21, whereby the distal portion of the convex side 132 allows for outer portion 52 of conductive material 25 to extend laterally beyond an edge of jaws 21 and 23, along only a portion of jaws 21,23. Such a shape allows a user to clearly see the tissue being cut as the user views the target site along a longitudinal direction down the length of the device.

Figure 3E:
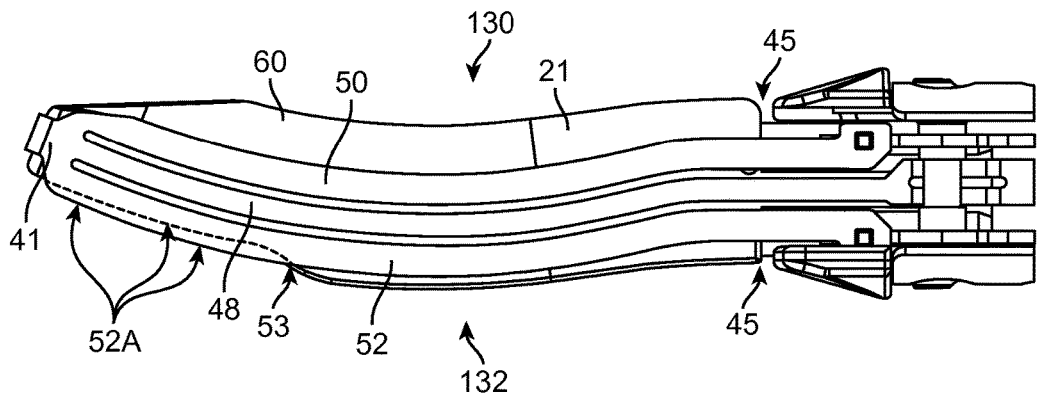
FIG. 3E shows an overhead view of the jaw of FIG. 3D in accordance with some embodiments.

FIG. 3E shows an overhead view of the jaw 21 of FIG. 3D without jaw 23, thereby providing full viewability to conductive material 25 in relation to jaw 21 of FIG. 3D. As shown, outer portion 52 of conductive material 25 has a distal portion 52a which at location 53, is allowed to extend beyond an outermost convex surface of jaw 21.

Figure 3F:
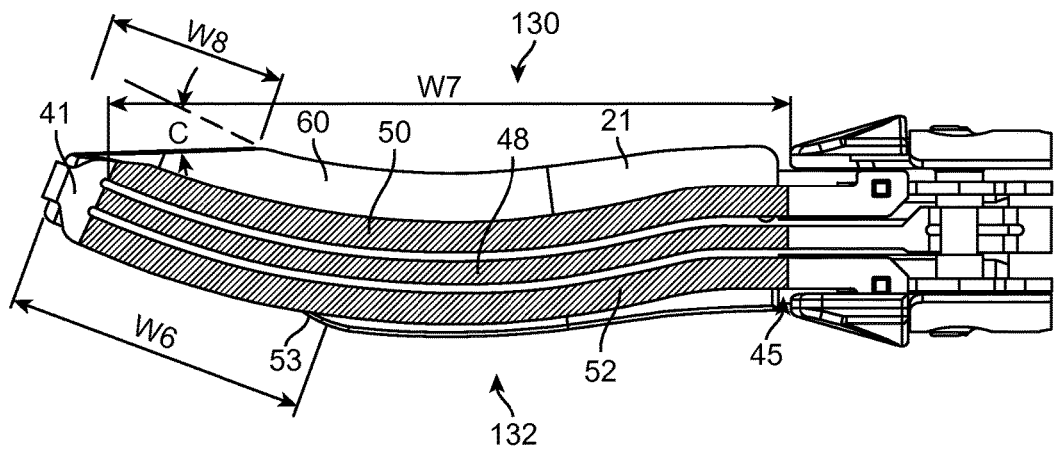
FIG. 3F shows a view similar to FIG. 3E, illustrating a cross-section of the conductive material taken through a plane parallel to and essentially bisecting the conductive material in accordance with some embodiments.

FIG. 3F shows a view similar to FIG. 3E, illustrating a cross-section of the conductive material 25 taken through a plane parallel to and essentially bisecting the conductive material 25. Illustrated in FIG. 3F are respective dimensions for portions of the jaws 21, 23. Conductive material 25 is shown to have a length W7 approximately 0.6 inches when measured from the distal end of clevises 85, 87, to a distal region of conductive material 25. This length can be modified as appropriate for the application of interest in which the surgical device is to be used for. Additionally, a distal portion of the concave portion of the jaws 21,23 is tapered at an angle C, wherein C is between ten and forty degrees. The tapered distal area allows for jaws 21,23 to abut against the main vessel 142 when positioned generally parallel and adjacent to the main vessel, than would otherwise would be possible.

Figure 4:
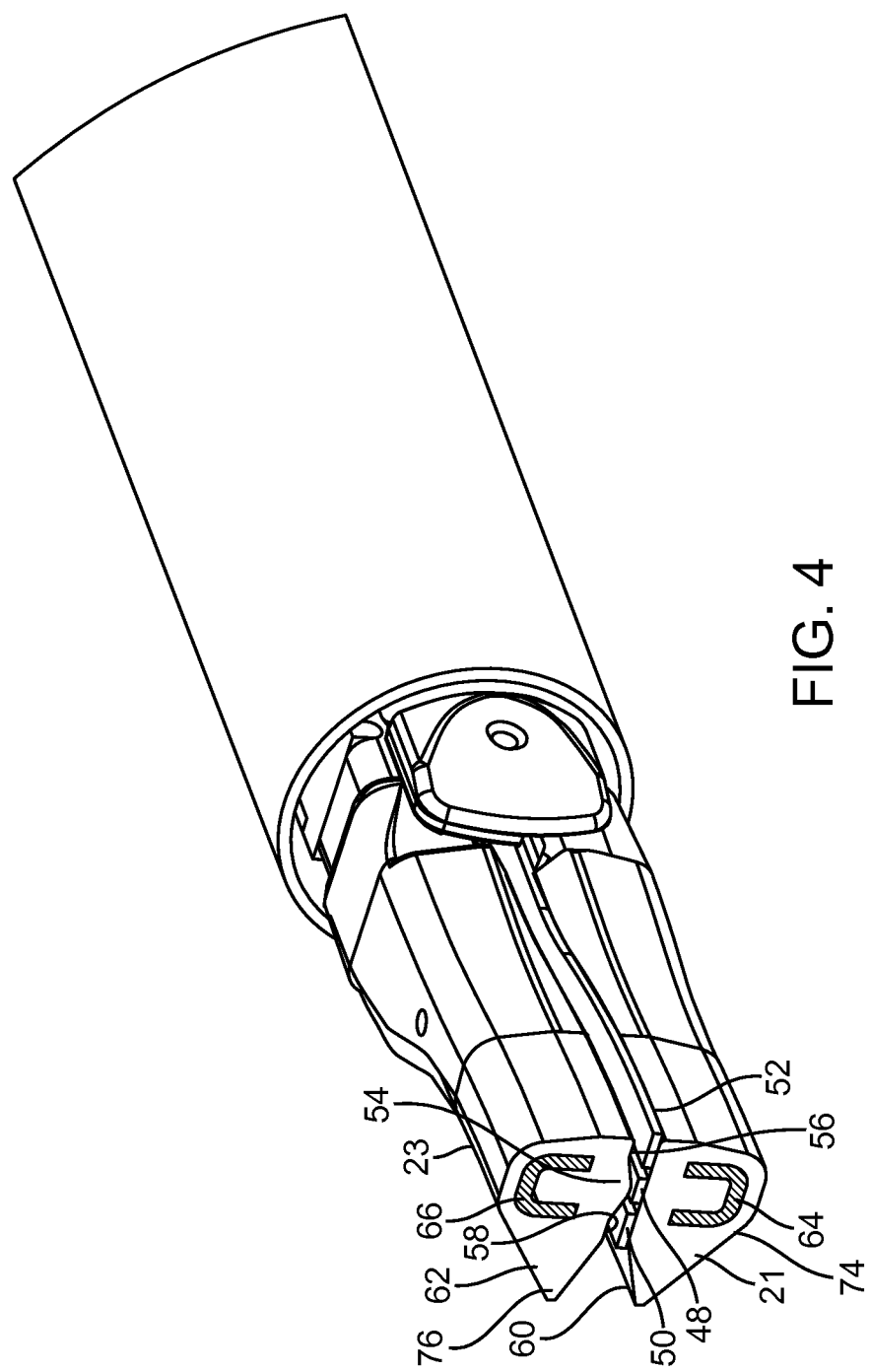
FIG. 4 is a perspective cross sectional view of the pair of jaws of FIG. 2 in accordance with some embodiments.

Referring now to FIG. 4, there is shown a partial cross sectional perspective view of the jaws 21, 23 that illustrates the placement of inner and outer portions 48, 50, 52. The jaw 21 includes a structural support 64, and the jaw 23 includes a structural support 66. The supports 64, 66 may be made from materials such as ceramic, polymers, stainless steel, or other metals or alloys. In some embodiments, the structural supports 64, 66 may be made from electrically conductive material that allows the supports 64, 66 to function as electrical lines (e.g., for transmitting current, RF signal, etc.). The structural supports 64, 66 are integrated with respective volumes 74, 76 of electrically insulating material, such as rubber, polymers, silicone, polycarbonate, ceramic or other suitable insulating material. As shown in the figure, the jaw 23 includes a surface elevation (protrusion) 54 substantially in alignment with the inner (middle) portion 48 in order to increase the compression force applied to a tissue structure grasped by the jaws 21, 23 and in contact with the middle portion 48. This promotes more efficient tissue severance, while adjacent regions 56, 58 of lower surface elevations on jaw 23 in alignment with the outer portions 50, 52 of the heating element introduce less compression force suitable for welding grasped tissue.

Figure 5A:
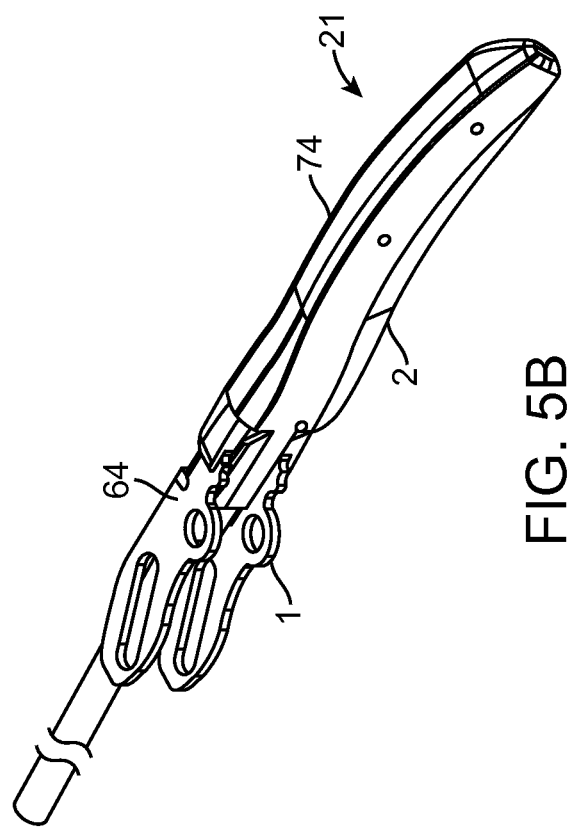
FIG. 5A illustrates a perspective view of a support structure for a jaw in accordance with some embodiments.
Figure 5B:
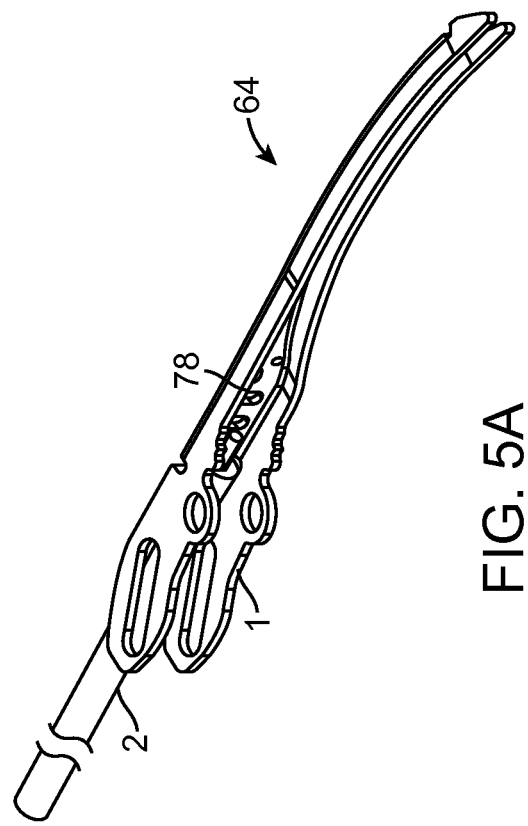
FIG. 5B illustrates a perspective view of a jaw, showing an insulative element integrated into the support structure of FIG. 5A.

FIG. 5A illustrates the support 64 of the jaw 21 in accordance with some embodiments. As shown in the figure, the structural support (support) 64 includes a plurality of through openings 78. Such configuration allows the layer of electrically insulating material (layer) 74 to be over-molded onto the support 64 (FIG. 5B). In particular, during the molding process for the layer 74, part of the material of the layer 74 will flow through the openings 78. When the molding material solidifies, the molding material within the openings 78 will be integrally formed with the rest of the layer 74 on both sides of the support 64, thereby forming a mechanical interlock (e.g., an anchor). This allows the layer 74 to be secured relative to the support 64 by mechanical engagement between the layer 74 and the support 64. In some cases, such a technique obviates the need to form the layer 74 separately and then to secure the layer 74 to the support 64 using an adhesive. Such a mechanical interlock also allows the layer 74 to remain mechanically secured relative to the support 64 when the jaw 21 is heated to elevated temperatures during use, which is more durable than bonding the layer 74 to the support 64 using an adhesive because the adhesive may fail due to high temperature. In the illustrated embodiments, the support 64 has a plurality of openings 78 that are disposed along the length of the support 64. This allows the layer 74 to be mechanically secured to the support 64 along its entire length. In other embodiments, the support 64 may include openings 78 at only certain region(s), such as the end(s), and/or the center, of the support 64. In further embodiments, instead of having a plurality of openings 78, the support 64 may include only one single opening 78. It should be noted that the opening(s) 78 may have different shapes in different embodiments, and therefore, should not be limited to the example of the shape shown. For example, in some cases, when the support 64 has a single opening 78, the opening 78 may have an elongated shape that extends along a length of the support 64. Also, in further embodiments, the openings 78 at the support 64 may have different shapes and/or sizes. Also, in other embodiments, the end section of the support 64 may have a tubular configuration (such as one having a circular, elliptical, rectangular, etc., cross-section), or may have a block configuration.

The jaw 23 may have a similar configuration as that of the jaw 21. FIG. 6A illustrates the structural support (support) 66 of the jaw 23 in accordance with some embodiments. As shown in the figure, the support 66 includes a plurality of through openings 80. Such configuration allows the layer of electrically insulating material (layer) 76 to be over-molded onto the support 66 (FIG. 6B). In particular, during the molding process for the layer 76, part of the material of the layer 76 will flow through the openings 80. When the molding material solidifies, the molding material within the openings 80 will be integrally formed with the rest of the layer 76 on both sides of the support 66, thereby forming a mechanical interlock (e.g., an anchor). This allows the layer 76 to be secured relative to the support 66 by mechanical engagement between the layer 76 and the support 66. In some cases, such a technique obviates the need to form the layer 76 separately and then to secure the layer 76 to the support 66 using an adhesive. Such a mechanical interlock also allows the layer 76 to remain mechanically secured relative to the support 66 when the jaw 23 is heated to elevated temperatures during use, which is more durable than bonding the layer 76 to the support 66 using an adhesive because the adhesive may fail due to high temperature. In the illustrated embodiments, the support 66 has a plurality of openings 80 that are disposed along the length of the support 66. This allows the layer 76 to be mechanically secured to the support 66 along its entire length. In other embodiments, the support 66 may include openings 80 at only certain region(s), such as the end(s), and/or the center, of the support 66. In further embodiments, instead of having a plurality of openings 80, the support 66 may include only one single opening 80. It should be noted that the opening(s) 80 may have different shapes in different embodiments, and therefore, should not be limited to the example of the shape shown. For example, in some cases, when the support 66 has a single opening 80, the opening 80 may have an elongated shape that extends along a length of the support 66. Also, in further embodiments, the openings 80 at the support 66 may have different shapes and/or sizes.

In other embodiments, instead of providing the openings 78, 80, the layers 74, 76 may be molded separately, and are then bonded onto the respective structural supports 64, 66. Also, in any of the embodiments described herein, the jaws 21, 23 may be coated with any number of materials to enhance their thermal and non-stick properties.

Figure 7A:
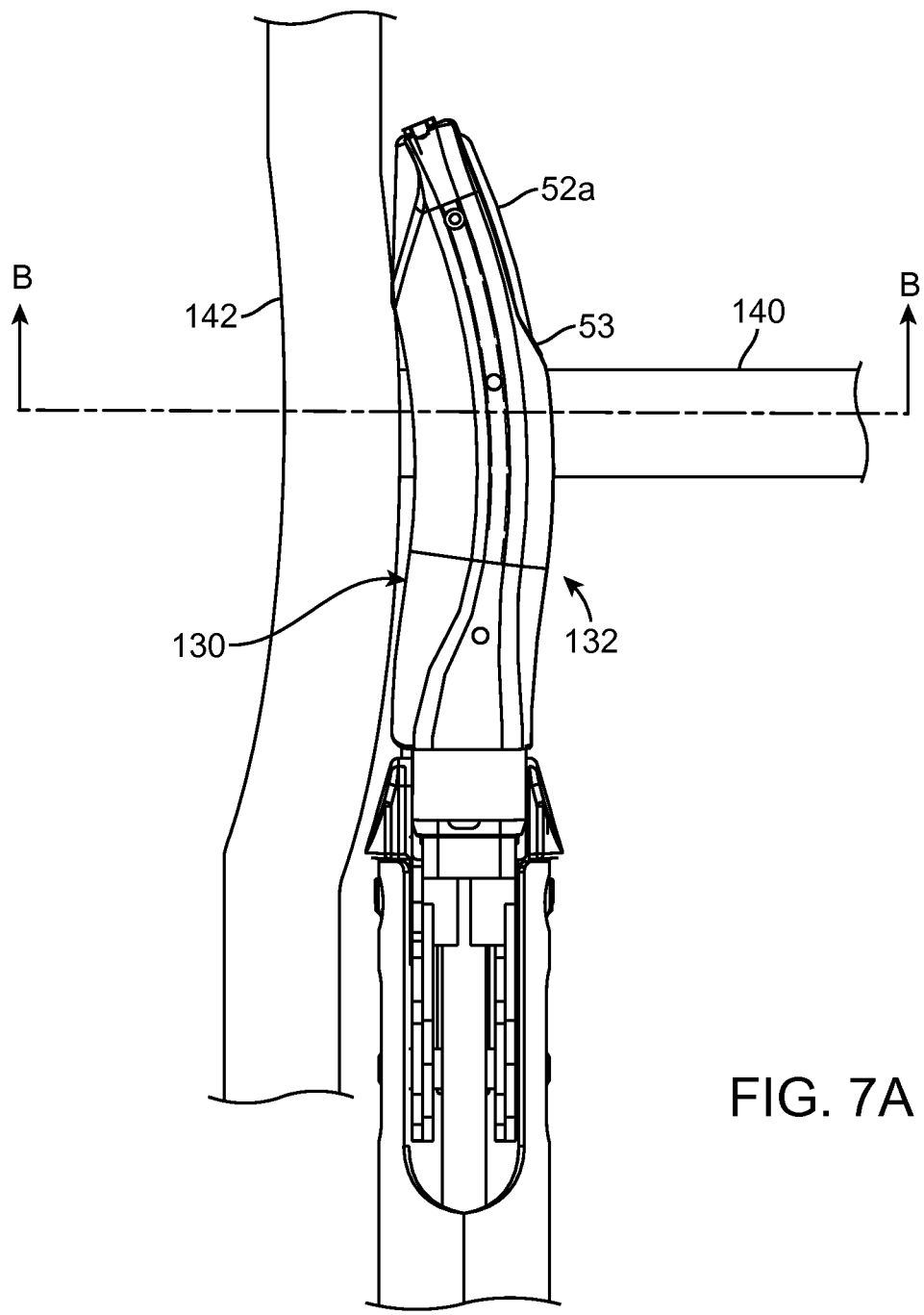
FIG. 7A is an overhead view of the pair of jaws of FIG. 2, showing the jaws being used to cut and seal a side branch vessel from a main vessel.
Figure 7B:
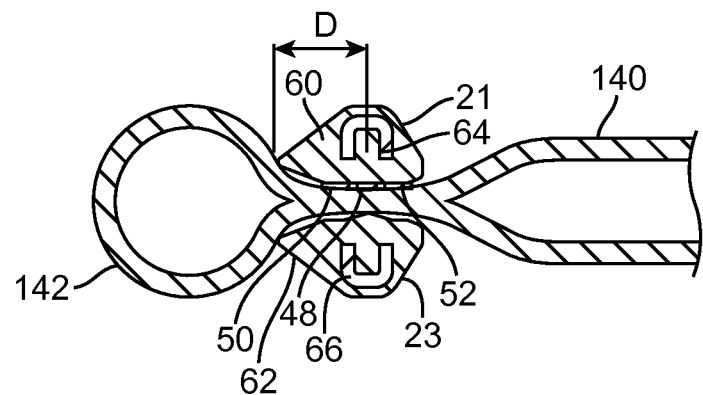
FIG. 7B is a cross sectional view of the pair of jaws of FIG. 7A taken through lines B-B, showing the jaws being used to cut and seal a side branch vessel from a main vessel.

In the illustrated embodiments, the cross sections of the respective jaws 21, 23 are not symmetrical. As shown in FIG. 7B, which is a cross sectional view of the embodiment shown in FIG. 7A, jaw 21 has a tapered protrusion 60, and jaw 23 has a tapered protrusion 62, each extending from a center location of the jaw and tapering in a direction lateral to the jaws and towards the concave portions 130. Each of the protrusions 60, 62 has a length so that when the protrusions 60, 62 abut a main vessel 142, the cutting point of the side branch vessel 140 is at a prescribed distance D that is branching from and spaced away from the main vessel 142 (FIG. 7B). In the illustrated embodiments, the distance D is at least 1 mm, and more preferably, at least 1.5 mm. In other embodiments, the distance D may have other values, such that distance D is sufficient to prevent or minimize thermal spread from electrode 25 to the main vessel 142 (or target structure) being harvested. As illustrated in the embodiments, the protrusions 60, 62 are advantageous in that they help prevent or minimize thermal spread to the main vessel 142 from the cutting and sealing of the side branch vessel 140, thereby preserving the integrity of the main vessel 142 that is being harvested. Also, the protrusions 60, 62 obviate the need for an operator to guess whether the location of the cut of the side branch vessel 140 is sufficiently far (e.g., beyond a minimum prescribed spacing) from the main vessel 142. Instead, the operator merely abuts the protrusions 60, 62 of the jaw assembly against the main vessel 142, and the protrusions 60, 62 will automatically place the jaw assembly relative to the side branch vessel 140 so that the side branch vessel 140 is cut at a minimum prescribed distance D from the main vessel 142. In some cases, if the surgical instrument 9 is used to cut other types of tissue, such as nerves, organs, tendons, etc., the protrusions 60, 62 also provide the same benefits of preserving the integrity of tissue adjacent to the cut, and obviating the need for a user to guess the appropriate margin. As shown in the figure, the protrusions 60, 62 diverge away from part of the side branch vessel 140. Such a configuration allows part of the side branch vessel 140 that is immediately next to the main vessel 142 not to be clamped by the jaws. As a result, the severed end of the side branch vessel 140 will fall away once it is cut. In other embodiments, the surgical instrument 9 does not need to include both protrusions 60, 62. Instead, the surgical instrument 9 includes either protrusion 60 or protrusion 62. Such configuration allows the device at the distal end of the instrument 9 to have a smaller profile, thereby allowing a user to effectively maneuver the distal device in tight tissue conditions. As shown in the figure, the outer portion 52 protrudes laterally along an outer edge of the closed jaws 21, 23. Such a configuration allows the outer portion 52 to deliver energy from the side of the jaw assembly even when the jaw assembly is closed. This allows the outer portion 52 to heat tissue from a side of the jaw assembly during an operation, such as for control of bleeding from the wall of the surgical cavity (tunnel).

Figure 7C:
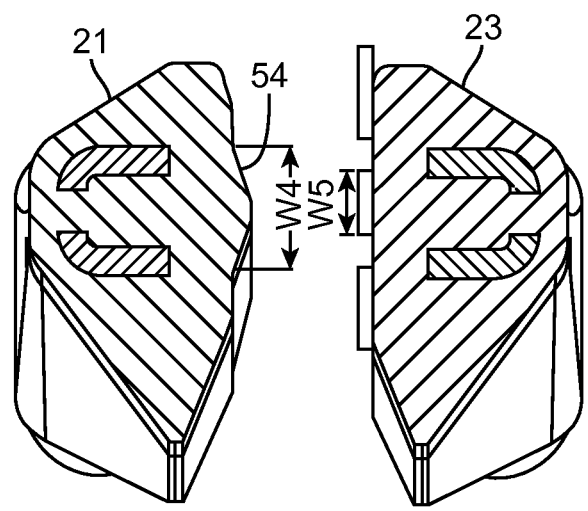
FIG. 7C illustrates another cross sectional view of the pair of jaws in accordance with other embodiments.

As shown in FIG. 3A, the jaw assembly has a concave side 130 and a convex side 132. In one method of use, while the jaw assembly is used to cut a side branch vessel 140, the jaw assembly is oriented so that its concave side faces towards the main vessel 142. The endoscope or viewing device is placed next to the jaw assembly with the endoscope or viewing device viewing the concave side of the jaw assembly. This allows the user to better visualize the tip of the jaw assembly. Such configuration also provides a safety benefit by allowing the user to know where the tips are during the vessel cutting procedure. Also as shown in FIGS. 3A, 4, and 7, the exposed outer portion 52 is on the convex side of the jaw assembly while the protrusions 60, 62 are on the concave side of the jaw assembly. The concavity provides extra spacing to further protect the main vessel 142 when the side branch vessel 140 is grasped. Furthermore, the exposed outer portion 52 on the convex side creates a protrusion that makes it easier to contact the wall of the tunnel with the exposed outer portion 52 to address bleeding. In other embodiments, the protrusions 60, 62 are on the convex side of the jaw assembly while the exposed outer portion 52 is on the concave side. In such cases, during use, the convex side 130 of the jaw assembly would be oriented towards the main vessel 142, thereby ensuring that the tips of the jaw assembly are separated from the main vessel 142 to enhance protection (e.g., preventing the tip of the jaw assembly from touching or injuring the main vessel 142).

Figure 8:
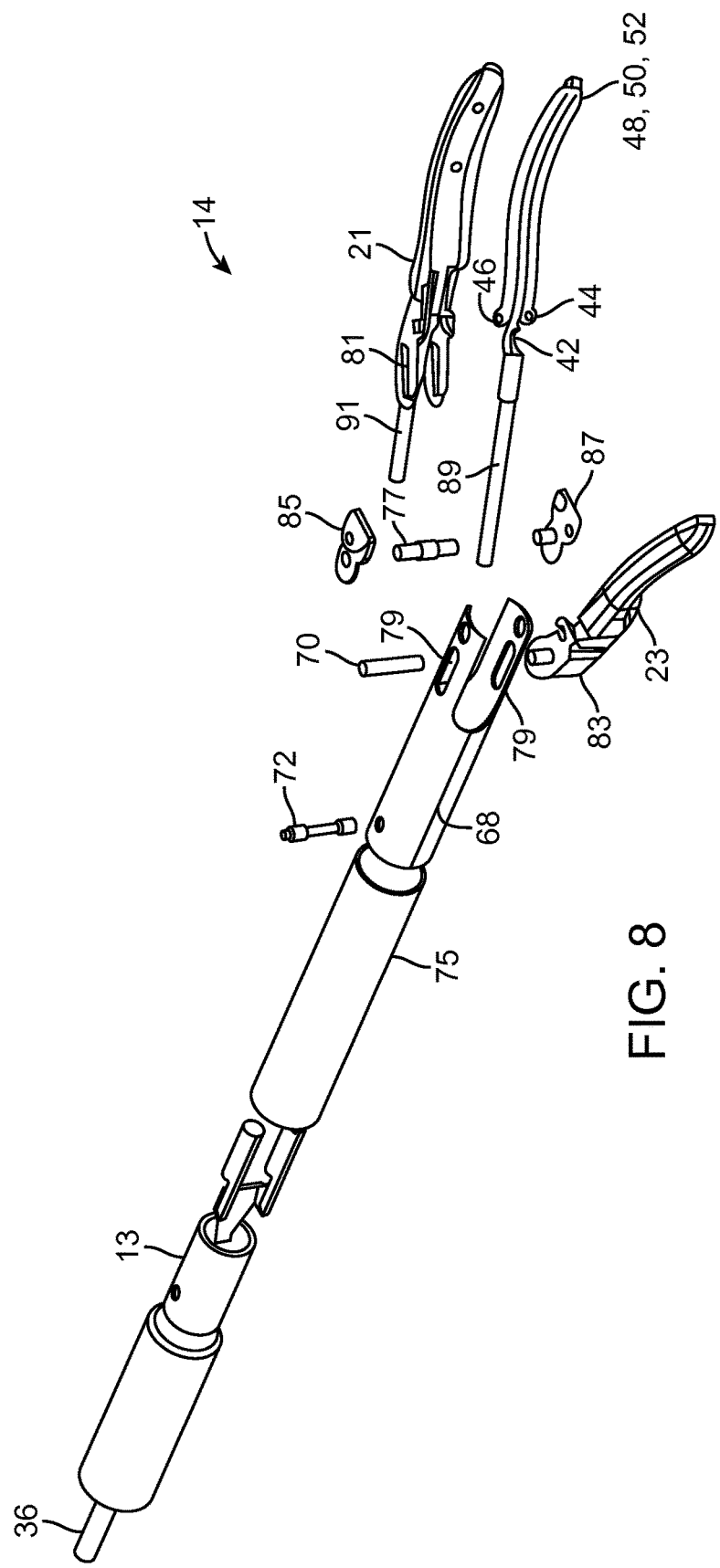
FIG. 8 is a partial exploded view of the components of a surgical instrument in accordance with some embodiments.

Referring now to FIG. 8, there is illustrated an exploded view of the components forming the surgical device 14, and its attachment to the distal end of the elongated body 13.

Specifically, the inner and outer portions 48, 50, 52 (electrically conductive material 25) are attached to jaw 21. Both jaws 21, 23 are pivotally attached via insulating material clevises 85 and 87 and pin 77 to the metal housing 68. The jaws 21,23 pivot on the clevises 85, 87 so that they can be kept electrically isolated from pin 77 which holds inner terminal 42 against the face of jaw 21. Such a configuration prevents the jaws 21, 23 from contacting the pin 77, avoiding an electrical short circuit. Pin 70 is disposed to slide within the aligned slots 79, and within the mating angled slots 81, 83 in the structural supports 64, 66 of the associated jaws to effect scissor-like jaw movement between open and closed positions as the slide pin 70 is moved relative to the pivot pin 77. Actuator rod 36 is linked to the slide pin 70, for example, via a yoke 37 that is attached to the distal end of the actuator rod 36. Axial movement of the actuator rod 36 in one direction will cause the slide pin 70 to move towards the pin 77, thereby opening the jaws 21, 23. Axial movement of the actuator rod 36 in the opposite direction will cause the slide pin 70 to move away from the pin 77, thereby closing the jaws 21, 23. An electrical conductor 89 connects to the inner terminal 42 of the inner and outer portions 48, 50, 52, and the outer terminals 44, 46 are electrically connected in common to conductor 91. In some embodiments, either conductor 89 or 91 may be housed within the wall or the bore of the elongated body 13. In other embodiments, if the actuator rod 36 is electrically conductive, either conductor 89 or 91 may be coupled to the actuator rod 36. In such cases, the actuator rod 36 will be electrically coupled to one terminal of the DC source 30, or to the contact 95 of the switch 78, during use. During use, the conductors 89, 91 are electrically coupled to terminals of the DC source 30, which provides a current to thereby heat up the inner and outer portions 48, 50, 52. The center heating element 48 is configured to cut a vessel (e.g., a side branch vessel) while the outer portions 50, 52 are configured to weld (seal) the vessel. In some embodiments, parts of the surgical device 14 may be insulated via an outer insulating layer for isolating certain components from biologic tissue and fluids.

During use of the surgical instrument 9, the elongated body 13 is advanced along a vessel to be harvested. In some cases, the instrument 9 may be placed into an instrument channel of a cannula, which includes a viewing device, such as an endoscope, for allowing an operator to see the distal end of the instrument 9 inside the patient. When a side branch vessel (or other target tissue) is encountered, the jaws 21, 23 grasp and compress the side branch vessel in response to manual manipulation of the actuator 15. Power is then supplied using the DC source 30 to the inner and outer portions 48, 50, 52 (which function as resistive element that heats up in response to the delivered direct current) to effect tissue welds at tissues that are in contact with outer portions 50, 52, and to effect tissue cutting at tissue that is in contact with inner portion 48.

During the vessel harvesting procedure, if the operator notices that there is bleeding in the surrounding tissues (e.g., from the walls of the surgical cavity), the operator may use the exposed portion of the outer portion 52 as a cauterizing electrode for controlling bleeding. For example, the side or the tip of the outer portion 52 that extends beyond the profile of the jaw assembly may be used to perform thermal spot cauterization by direct thermal conduction. In such cases, the outer portion 52 is heated, and its exposed edge (or tip) is used to touch tissue that is desired to be cauterized.

In any of the embodiments described herein, the surgical instrument 9 may include a power control for controlling a delivery of power to the electrode 25. For example, in some embodiments, the surgical instrument 9 may further include a control module 32, such as that shown in FIG. 1, for controlling a delivery of power to the electrode 25. In the illustrated embodiments, the control module 32 is located within the energy source 30. In other embodiments, the control module 32 may be coupled to the energy source 30, or to other components of the surgical instrument 9. The control module 32 may be implemented using hardware, software, or a combination thereof. In some embodiments, the control module 32 may include a processor and a medium, such as a volatile or a non-volatile medium, for storing data. The medium may be used to store any of the variables and/or parameters described herein.

Figure 9:
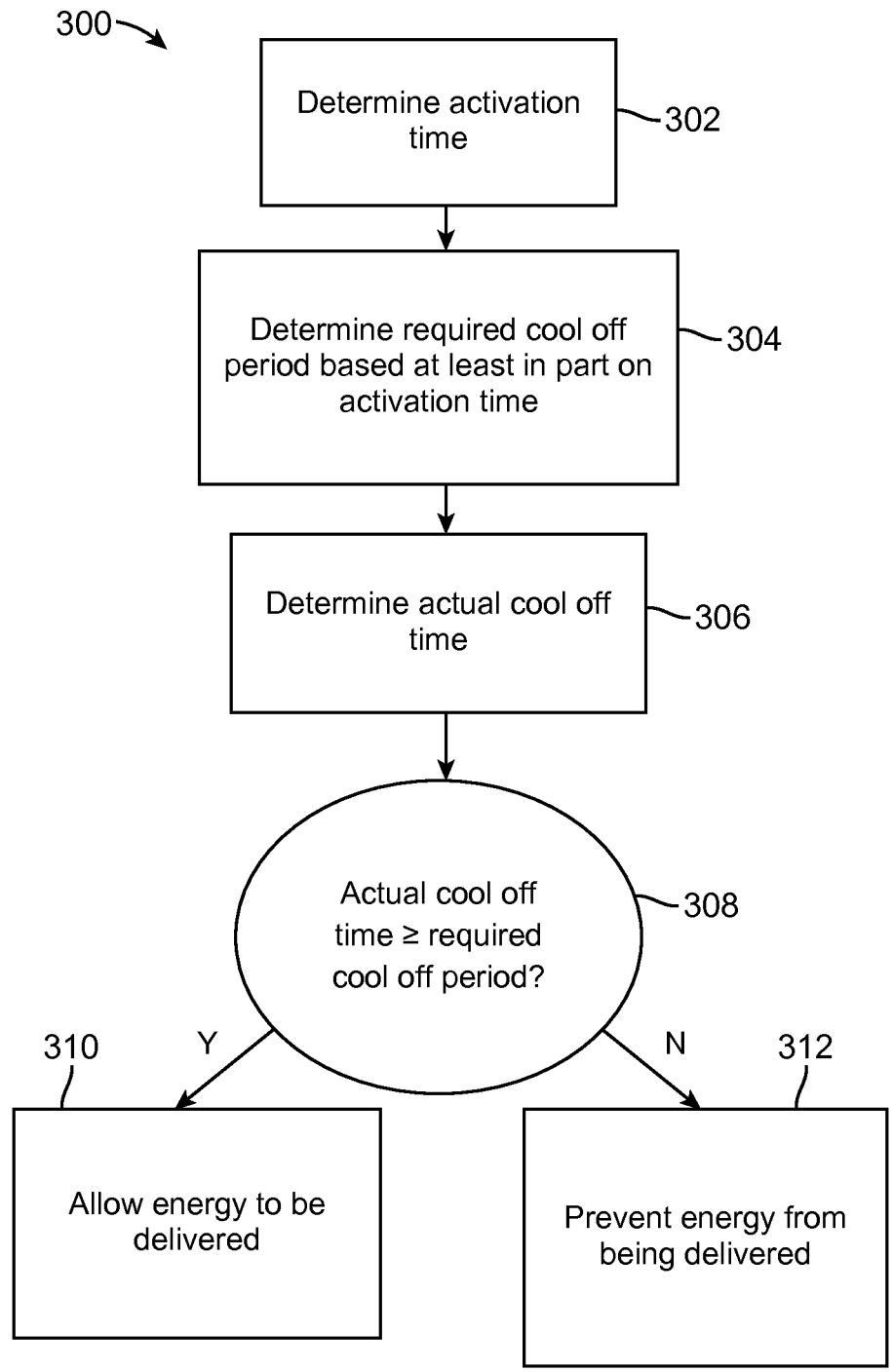
FIG. 9 illustrates a method for controlling a delivery of power for the surgical instrument of FIG. 1 in accordance with some embodiments.

In some embodiments, the control module 32 is configured to allow or prevent power to be delivered to the electrode 25 when a certain prescribed condition is satisfied. FIG. 9 illustrates a method 300 that may be performed by the control module 32 in accordance with some embodiments. During use of the surgical instrument 9, the electrode 25 is energized by actuating the actuator 15 at the handle 11 to deliver heat, such as to cut and/or severe vessel tissue. When this occurs, the control module 32 then keeps track with the amount of time for which the electrode 25 is energized (Step 302). In some cases, the determined activation duration is stored in a medium for later processing.

When the actuator 15 is de-actuated to stop the energy source 30 from delivering further energy to the electrode 25, the control module 32 then determines a required cool off period based at least in part on the activation duration (Step 304). In the illustrated embodiments, the longer that the electrode 25 is activated, the longer the cool off period that is required, and vice versa. The required cool off period may be determined by the control module 32 using a function that represents a relationship between the activation period and the required cool off period. Alternatively, a look up table stored in the medium may be used by the control module 32 to determine the required cool off period. In some cases, when the activation time of the electrode 25 reaches an activation duration threshold, then a minimum required cool off time is imposed by the control module 32. In such cases, as the activation time of the electrode 25 extends beyond the activation duration threshold, the required cool off time is increased by the control module 32 in accordance with a predetermined function (such as a linear function, or a non-linear function). In other embodiments, if the activation time for the electrode 25 is less than a prescribed minimum activation time, then the control module 32 will assume that no activation of the electrode 25 has occurred. Thus, the required cool off period may not be imposed by the control module 32 unless the electrode 25 was previously activated for at least a certain prescribed minimum period (or unless the electrode 25 has previously reached a certain prescribed temperature in other embodiments). Such a feature has the benefit of allowing the control module 32 to ignore short activation(s) of the electrode 25, thereby simplifying the analysis that needs to be performed by the control module 32. In further embodiments, the required cool off period may not be variable, and may be fixed to be a constant value instead.

In some embodiments, the control module 32 may be configured (e.g., built, constructed, programmed, etc.) to monitor a moving average of ON/OFF cycles that would more accurately reflect the temperature at the jaw assembly. The moving average may be the actual calculated average, a weighted moving average, or an exponential moving average. In some embodiments, the control module 32 may be configured to use a function to determine the moving average. The monitoring of the moving average may be performed by considering the ON/OFF cycles that have occurred within a prescribed period. For example, the moving average may be calculated within a moving window of 5 seconds. In such cases, if out of the past 5 seconds, the electrode was ON for the first second, it would have a lesser influence to activate the safety circuit than if it were ON for the last second of the past 5 seconds. The moving window may have other durations in other embodiments.

The control module 32 also keeps track of the time that has passed since the electrode 25 was de-activated (Step 306). In some embodiments, the control module 32 may include a timer for performing such a function. The tracked time represents a length of the actual cool off period since the previous activation of the electrode 25. The determined actual cool off period may be stored in a medium for later processing.

Next, the control module 32 compares the actual cool off period with the required cool off period (Step 308). If the actual cool off period is at least equal to the required cool off period, then the control module 32 allows energy to be delivered from the energy source 30 to the electrode 25 (Step 310). In some embodiments, the control module 32 allows the electrode 25 to be energized for a prescribed maximum duration. The prescribed maximum duration may be a fixed constant in some embodiments. In such cases, while the electrode 25 is energized, the control module 32 keeps track the amount of time for which the electrode 25 has been energized. When the activation duration for the electrode 25 reaches the prescribed maximum duration, the control module 32 then prevents the energy source 30 from delivering further energy to the electrode 25. In other embodiments, the prescribed maximum duration for which the electrode 25 is energized is a function of previous activation period(s) and/or previous cool off period(s). In other embodiments, the control module 32 allows activation of the electrode 25 until a temperature (measured using a temperature sensor at the jaw assembly) reaches a prescribed value. The prescribed duration or temperature value may be selected such that overheating of the jaw assembly is prevented. In other embodiments, the prescribed duration or prescribed temperature value may be a maximum duration or maximum temperature, respectively, below which tissue heating is desired. In further embodiments, the control module 32 allows activation of the electrode 25 until a condition of tissue being affected by the jaw assembly is achieved (e.g., tissue is severed, tissue is sealed, tissue reaches a temperature, tissue reaches an impedance value, etc.). The prescribed maximum duration for which the electrode 25 can be energized, or the prescribed temperature value, may be variable.

If the actual cool off period is less than the required cool off period, then the control module 32 prevents delivery of energy from the energy source 30 to the electrode 25 (Step 312). In some embodiments, the control module 32 prevents delivery of energy to the electrode 25 at least until the required cool off period is reached. Alternatively, or additionally, the control module 32 may prevent delivery of energy to the electrode 25 until a temperature (measured by a temperature sensor at the jaw assembly) is below a prescribed threshold.

In some embodiments, the control module 32 may be configured (e.g., programmed and/or constructed) to utilize a count up and count down technique to determine whether the electrode 25 is allowed to be activated, and/or how long the electrode 25 is activated. Such may be accomplished using a counter. For example, in some embodiments, when the electrode 25 is activated, the control module 32 then increments the value of the counter. As the electrode 25 is continued to be activated, the control module 32 continues to increment the value of the counter. When the user operates the actuator 15 at the handle to stop delivery of energy to the electrode 25, the control module 32 then decrements the value of the counter. In some embodiments, the control module 32 allows the electrode 25 to be energized as long as the counter value is below a prescribed activation threshold. Also, in some cases, the control module 32 may prevent the electrode 25 from being energized if the counter value reaches a prescribed maximum value. Also, in some embodiments, the difference between the prescribed maximum value for the counter and the actual counter value may be used to determine how long the electrode 25 may be activated.

It should be noted that the functions of allowing and preventing power to be delivered may be implemented using circuits and/or switches, which are known in the art of circuit design.

It should be noted that the order of the steps in method 300 may be different from that shown, and that in other embodiments, one or more of the steps in the method 300 may be combined. Also, in further embodiments, any of the steps in the method 300 may have sub-steps. In still further embodiments, any of the steps in the method 300 may be omitted.

In the above embodiments, the control module 32 is configured to allow or prevent activation of the electrode 25 based on time variables (e.g., duration of electrode activation, duration of cool off period, etc.). In other embodiments, the control module 32 may be configured to allow or prevent activation of the electrode 25 based on temperature. For example, in other embodiments, in step 302, the control module 32 may be configured to determine a temperature at the jaw assembly (e.g., using a temperature sensor). In such cases, the required cool off time period in step 304 may be determined based on the determined temperature. In some embodiments, the higher the temperature is at the jaw assembly, the longer the cool off time is required, and vice versa.

Figure 10:
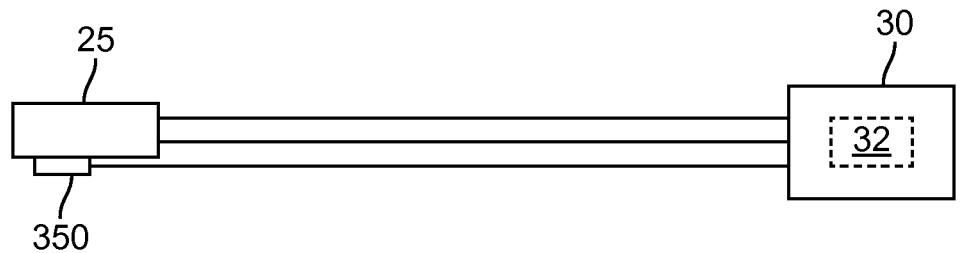
FIG. 10 illustrates portions of a surgical instrument having a temperature sensor in accordance with some embodiments.

FIG. 10 illustrates a circuitry connecting the electrode 25 to the energy source 30. Other components of the surgical instrument 9 are omitted for clarity purpose. As shown in the figure, the surgical instrument 9 includes a temperature sensor 350 coupled to the electrode 25. The temperature sensor 350 is used to sense temperature of the electrode 25 or of tissue that is being operated on by the jaw assembly. The temperature sensor 350 is communicatively coupled to the control module 32 so that sensed temperature data may be transmitted to the control module 32 for processing. In some embodiments, temperature data from the temperature sensor may be stored in a medium for later processing. The temperature sensor may be a thermocouple, a thermistor, or any of other devices that are capable of sensing a characteristic that corresponds with a temperature. In some embodiments, the temperature sensor may be embedded in the jaw assembly for sensing a temperature at the tissue contact surface of the electrode 25.

Figure 11:
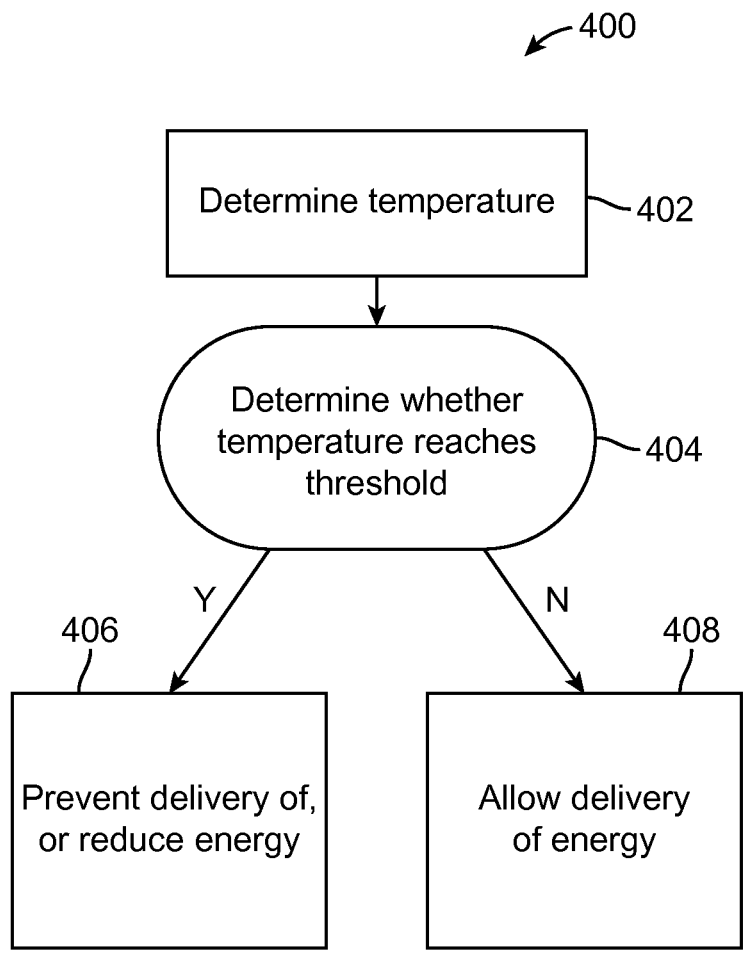
FIG. 11 illustrates another method for controlling a delivery of power for the surgical instrument of FIG. 1 in accordance with other embodiments.

FIG. 11 illustrates a method 400 that may be performed by the control module 32 of FIG. 10 to control a delivery of energy to the electrode 25 in accordance with other embodiments. During use of the surgical instrument 9, the user may activate the actuator 15 at the handle 11 to deliver energy from the energy source 30 to the electrode 25. The energized electrode 25 may be used to cut and/or seal a vessel that is being grasped by the jaw assembly. The temperature sensor 350 senses the temperature at the electrode 25, and transmits the temperature data to the control module 32. The control module 32 obtains the temperature data (Step 402), and is configured to determine whether the sensed temperature reaches a prescribed temperature threshold (Step 404). The temperature threshold may be selected such that it corresponds with the state at which a certain tissue condition (e.g., tissue transection, tissue welding, etc.) is reached, or the condition that the device is overheated.

If the sensed temperature reaches the prescribed temperature threshold, the control module 32 then causes the energy source 30 to either stop delivering energy to the electrode 25, or reduce the amount of energy being delivered to the electrode 25 (Step 406). The control module 32 may utilize any known technique and/or component(s) (such as electrical switches, mechanical switches, logics, etc.) for stopping delivery of energy and/or for reducing an amount of energy being delivered from an energy source. In some cases, the reduction of energy may be achieved by lowering the voltage at the energy source 30. Alternatively, the reduction of energy may be achieved by lowering the current being delivered to the electrode 25. In further embodiments, both the voltage and the current may be lowered to reduce the energy being delivered to the electrode 25.

On the other hand, if the sensed temperature has not reached the prescribed temperature threshold, the control module 32 then continues to allow delivery of energy from the energy source 30 to the electrode 25 (Step 408). In some embodiments, even if the determined temperature has not reached the prescribed temperature threshold, the control module 32 can still be configured to control the manner in which energy is being delivered to the electrode 25 based at least in part on the determined temperature. For example, the control module 32 may use time as a control factor to allow stages of voltage and/or current control (e.g., step up or down), thereby controlling the power output of the energy source 30. In some cases, if the sensed temperature has not reached the prescribed temperature threshold, the control module 32 may cause the energy source 30 to increase its output (e.g., increase voltage, current, or both) to increase the temperature of the electrode 25 more quickly, thereby heating tissue in a more efficient manner.

In any of the embodiments described herein, absolute temperature (at any of the inner and outer portions 48, 50, 52), and/or temperature difference between inner portion 48 and outer portions 50, 52, may be achieved by voltage and/or current control, and design of the inner and outer portions 48, 50, 52 (heating elements). In other embodiments, the surgical instrument 9 does not include three electrode portions 48, 50, 52. Instead, the surgical instrument 9 includes an electrode 25 with a single operative portion. In such cases, the temperature at the electrode 25 may be achieved by voltage and/or current control, design of the electrode 25, and/or feedback resistance.

Figure 12:
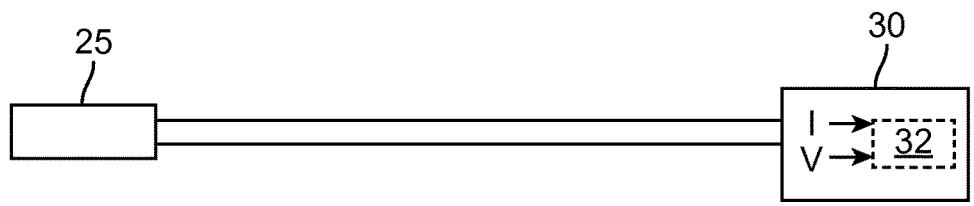
FIG. 12 illustrates portions of a surgical instrument having a control for controlling a delivery of power based at least in part on a voltage and a current in accordance with some embodiments.

In further embodiments, the control of the delivery of energy to the electrode 25 may be performed based at least in part on an electrical resistance of a material, such as the resistance of the electrode 25. In such cases, the electrode 25 acts as a thermistor. FIG. 12 illustrates a circuitry connecting the electrode 25 to the energy source 30 in accordance with other embodiments. Other components of the surgical instrument 9 are omitted for clarity purpose. As shown in the figure, voltage and current associated with the operation of the electrode 25 may be obtained from the energy delivery circuitry. The voltage and current may be processed by the control module 32 to determine an electrical resistance value, which may represent an electrical resistance of the electrode 25. Techniques for calculating electrical resistance using voltage and current are well known in the art. In some embodiments, the sensed voltage and current may be stored in a medium for later processing by the control module 32.

Figure 13:
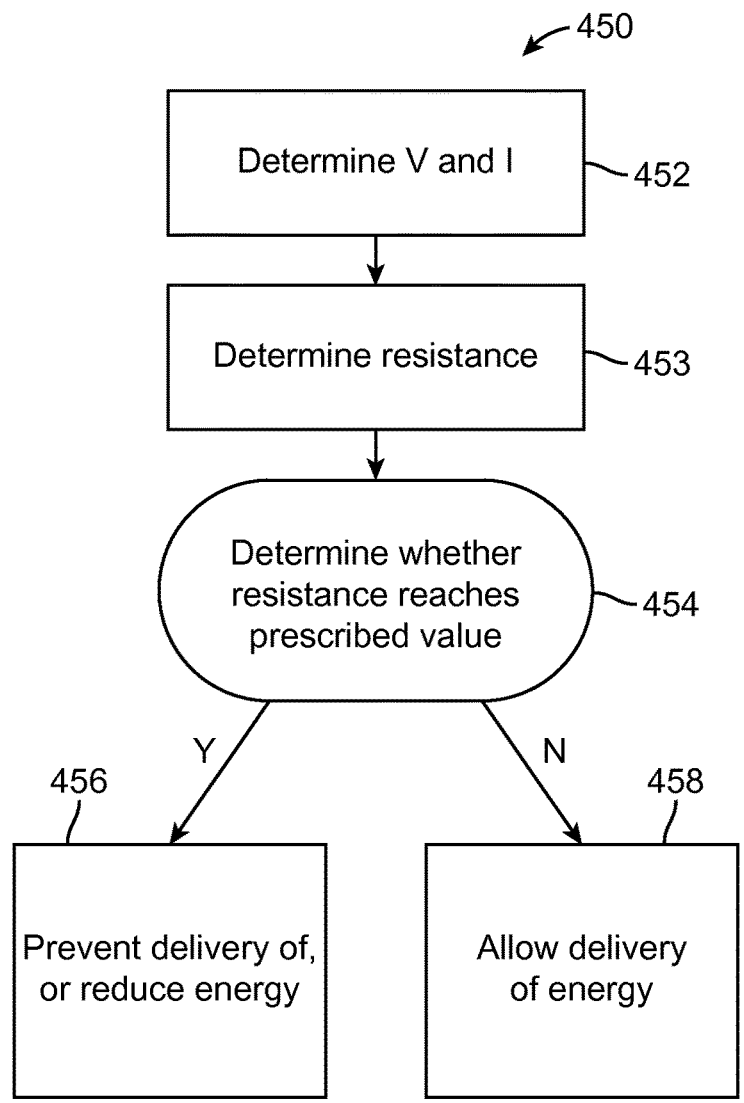
FIG. 13 illustrates another method for controlling a delivery of power for the surgical instrument of FIG. 1 in accordance with other embodiments.

FIG. 13 illustrates a method 450 that may be performed by the control module 32 of FIG. 12 to control a delivery of energy to the electrode 25 in accordance with other embodiments. During use of the surgical instrument 9, the user may activate the actuator 15 at the handle 11 to deliver energy from the energy source 30 to the electrode 25. The energized electrode 25 may be used to cut and/or seal a vessel that is being grasped by the jaw assembly. While the electrode 25 is energized, voltage and current associated with the delivery of energy to the electrode 25 may be determined from the energy delivery circuitry. Techniques for obtaining voltage and current from an energy delivery circuitry are well known in the art. The control module 32 obtains the voltage and current values (Step 452), and determines an electrical resistance value using the voltage and current values (Step 453).

Figure 14:
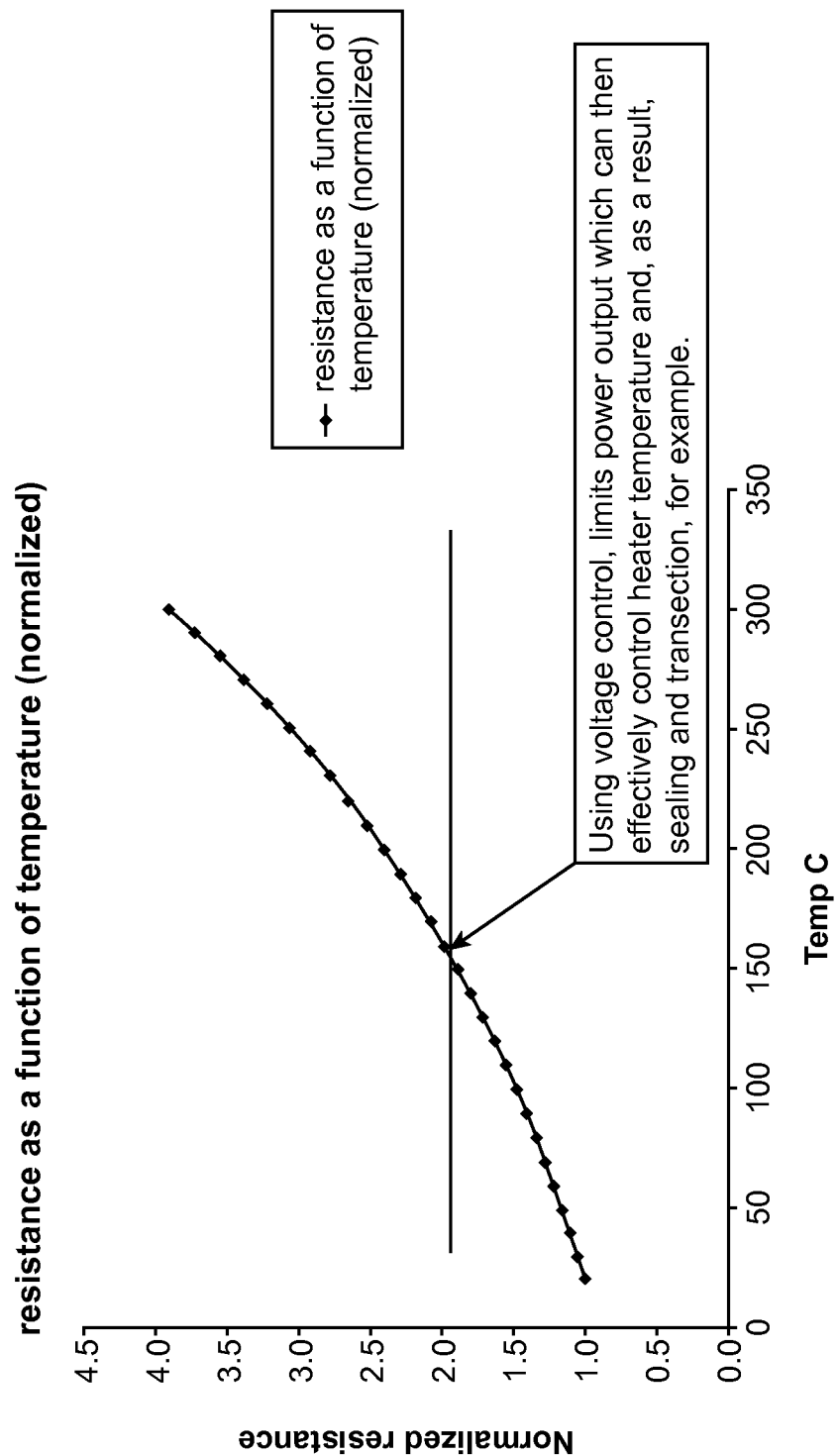
FIG. 14 is a graph illustrating how a material's resistance may vary with temperature.

In the illustrated embodiments, the determined electrical resistance may correspond with certain conditions of the electrode 25, such as the temperature of the electrode 25. In particular, with knowledge of the resistance of the electrode 25 at a given temperature, and how the resistance changes with temperature, one could determine the temperature of the electrode 25 given the voltage and current flowing through the energy delivery circuit. FIG. 14 is a graph illustrating how a resistance of a material may vary with temperature. Thus, by determining the resistance and how the resistance changes, the control module 32 can determine the temperature of the electrode 25. Such a feature is advantageous in that it obviates the need to use a temperature sensor in the jaw assembly of the surgical instrument 9.

Returning to FIG. 13, the control module 32 next determines whether the resistance value reaches a prescribed electrical resistance value (Step 454). The prescribed electrical resistance value may be selected such that it corresponds to a certain temperature at the jaw assembly. For example, the prescribed electrical resistance may correspond to a temperature at the jaw assembly at which tissue transection, and/or tissue sealing may occur. In other embodiments, the prescribed electrical resistance may correspond to a temperature at the jaw assembly at which the device may be overheated.

If the determined resistance value reaches the prescribed resistance value, the control module 32 then causes the energy source 30 to either stop delivering energy to the electrode 25, or to reduce the amount of energy being delivered to the electrode 25 (Step 456). The control module 32 may utilize any known technique and/or component(s) (such as electrical switches, mechanical switches, logics, etc.) for stopping delivery of energy and for reducing an amount of energy being delivered from an energy source. In some cases, the reduction of energy may be achieved by lowering the voltage while maintaining a constant current at the energy source 30. Alternatively, the reduction of energy may be achieved by lowering the current being delivered to the electrode 25 while maintaining a constant voltage. In further embodiments, both the voltage and the current may be lowered to reduce the energy being delivered to the electrode 25. In further embodiments, the energy delivery to the electrode 25 may be controlled (e.g., stopped or slowed down) such that tissue is heated in a desired manner (such as to accomplish tissue cutting and/or welding at the vessel).

On the other hand, if the determined electrical resistance has not reached the prescribed resistance value, the control module 32 then continues to allow delivery of energy from the energy source 30 to the electrode 25 (Step 458). In some embodiments, even if the determined electrical resistance has not reached the prescribed resistance value, the control module 32 can still be configured to control the manner in which energy is being delivered to the electrode 25 based at least in part on the determined resistance value (or voltage and/or current from the energy delivery circuit). For example, the control module 32 may use time as a control factor to allow stages of voltage and/or current control (e.g., step up or down), thereby controlling the power output of the energy source 30. In some cases, if the resistance has not reached the prescribed resistance value, the control module 32 may cause the energy source 30 to increase its output (e.g., increase voltage, current, or both) to increase the temperature of the electrode 25 more quickly, thereby heating tissue in a more efficient manner.

In other embodiments, instead of using temperature and resistance, the surgical instrument 9 may utilize other types of parameters for allowing the control module 32 to control the delivery of energy from the energy source 30. For example, in other embodiments, the surgical instrument 9 may include a fine gauge fiber that is placed at the distal end of the device (e.g., at the jaw assembly). The fiber is used to transmit infrared spectrum waves to a receiver that is configured to determine temperature based at least in part on the signature of the infrared spectrum. In this case, the control module 32 may include the receiver, and is configured to control the delivery of energy based on the determined temperature.

In further embodiments, the surgical instrument 9 may use pulse width modulation to control heat output based on lookup time tables or heater circuit resistance measurements. For example, the control module 32 may be configured to use time as a control factor to allow stages of power pulse modulation and step up or down the length of time the power is delivered as a function of time. Alternatively, the control module 32 may use resistance as a mechanism to infer heating element surface temperature (e.g., based on experimental or calculated data that are dependent on the material), and uses that inference to control the power output.

In any of the embodiments described herein, the control mechanism of the control module 32 may be implemented using coded logic and/or analog circuit design, which are techniques well known in the art. Also, in any of the embodiments described herein, the control module 32 may directly control (e.g., by actuating a solid state switch or other mechanism, etc.), or indirectly control (e.g., via a relay or similar mechanism) the power circuit. The control module 32 may also be used to modulate power based at least in part on a predefined control pattern associated with a length of time the device is actuated (as described herein). Also, in any of the embodiments described herein, the control module 32 may be configured for allowing/preventing an additional power source to deliver power to the device.

Figure 15:
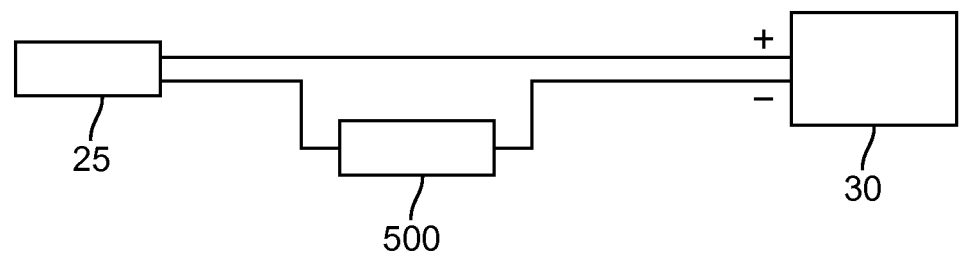
FIG. 15 illustrates portions of a surgical instrument having a positive temperature coefficient device in accordance with some embodiments.

FIG. 15 illustrates another technique for controlling a delivery of power to the electrode 25 of the surgical instrument 9 in accordance with other embodiments. The figure shows the circuitry connecting the electrode 25 to the energy source 30. Other components of the surgical instrument 9 are omitted for clarity purpose. As shown in the figure, the surgical instrument 9 includes a positive temperature coefficient (PTC) device 500 that is coupled to a current line that is connected to the negative terminal of the energy source 30. In other embodiments, the PTC device 500 may be coupled to the current line that is connected to the positive terminal of the energy source 30. The PTC device 500 is configured to allow a current to be delivered therethrough when the PTC device's temperature is below a prescribed level. When the temperature of the PTC device 500 reaches the prescribed level, the PTC device 500 will prevent the current from being delivered therethrough, thereby preventing delivery of power to the electrode 25.

In some embodiments, the PTC device 500 includes conductive particles that are dispersed in a material. The conductive particles contact each other to form a conductive path in the material when the temperature of the material is below a certain level. When the temperature of the material reaches a certain level, the material expands, thereby causing the conductive particles to separate from each other. This in turn prevents a current from going through the PTC device 500. When the PTC device 500 is sufficiently cooled, the material of the PTC device 500 contracts, thereby bringing the conductive particles together into contact with each other to form a conductive path. This in turn allows the PTC device 500 to conduct current therethrough.

In other embodiments, the PTC device 500 may include a bimetallic or other such element to control heat output or surface temperature in a specified range (or value) by opening or closing of the electrical circuit. For example, the PTC device 500 may include a bimetallic strip element, the operation of which is based on the difference in thermal expansion properties of two metals within the device. In particular, the thermal expansion of the two metals causes a displacement within the device that physically breaks the electrical connection temporarily. When the device is sufficiently cooled, the electrical connection is re-established.

In some embodiments, the properties of the PTC device 500 (such as the properties of the material containing the conductive particles, operating temperature, resistance-temperature profile, etc.) may be selected such that it provides a prescribed cooling time (which is dependent upon on how fast the material collapses) between activations of the electrode 25, and/or a prescribed maximum heating time (which is dependent upon on how fast the material expands) for an activation of the electrode 25. Also, in some embodiments, the properties of the PTC device 500 (such as the properties of the material containing the conductive particles) may be selected such that the PTC device 500 will prevent delivery of energy to the electrode 25 when a prescribed temperature is reached (which is dependent upon the thermal expansion property of the material housing the conductive particles). The prescribed temperature may be selected such that overheating of the jaw assembly is prevented. In other embodiments, the prescribed temperature may be a maximum temperature below which tissue heating is desired. In other embodiments, the PTC device 500 may prevent delivery of energy to a part of the electrode 25, thereby stopping the delivery of heat by the part of the electrode, and changing the thermal output profile.

Using the PTC device 500 to control a delivery of energy to the electrode 25 is advantageous because it does not require use of a temperature sensor, nor does it require a separate processor to process (e.g., analyze) sensed parameters.

As shown in the figure, the PTC device 500 is secured somewhere in the middle of the surgical instrument 9. In other embodiments, the PTC device 500 may be secured at other locations along the length of the surgical instrument 9, such as closer to, or at, the electrode 25. In further embodiments, the PTC device 500 may be secured near or at the energy source 30. In still further embodiments, the PTC device 500 may be coupled to the cable that connects the energy source 30 to the surgical instrument 9. In other embodiments, the PTC device 500 could also be in the power supply, and different power supplies could include different PTCs (or several PTCs with the option to select them).

In any of the embodiments, the PTC device 500 may directly control (e.g., by placing the PTC device 500 directly in the circuit), or indirectly control (e.g., via relay or similar mechanism) the power circuit. In further embodiments, the PTC device 500 may also be used for allowing or preventing an additional power source (e.g., a RF source) from delivering power to the electrode 25. In some embodiments, the PTC device 500 may be implemented as a part of the electrode 25.

Figure 16:
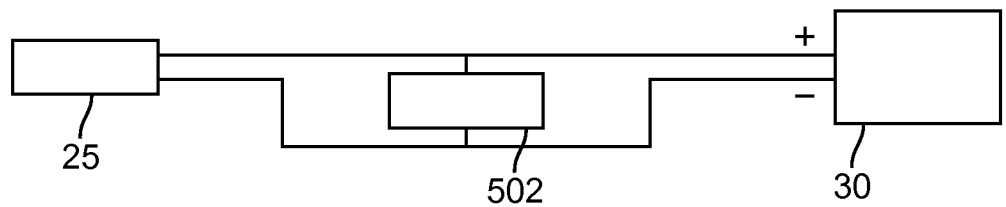
FIG. 16 illustrates portions of a surgical instrument having a negative temperature coefficient device in accordance with some embodiments.

FIG. 16 illustrates another technique for controlling a delivery of power to the electrode 25 of the surgical instrument 9 in accordance with other embodiments. The figure shows the circuitry connecting the electrode 25 to the energy source 30. Other components of the surgical instrument 9 are omitted for clarity purpose. As shown in the figure, the surgical instrument 9 includes a negative temperature coefficient (NTC) device 502 that is coupled between two current lines that are connected to the positive and negative terminals of the energy source 30, respectively. The NTC device 502 is configured to provide a relatively high electrical resistance when the NTC device 502 at a relatively low temperature. When the NTC device 502 is heated up, its electrical resistance decreases, thereby allowing a highly conductive path to be formed from the energy source 30 to the NTC, and then return to the energy source 30. This in turn will prevent energy from being delivered from the energy source 30 to the electrode 25. When the NTC device 502 is sufficiently cooled, the resistance of the NTC device 502 increases, thereby allowing current to be delivered to the electrode 25.

In some embodiments, the properties (e.g., material(s), operating temperature, resistance-temperature profile, etc.) of the NTC device 502 may be selected such that it provides a prescribed cooling time between activations of the electrode 25, and/or a prescribed maximum heating time for an activation of the electrode 25. Also, in some embodiments, the properties of the NTC device 502 may be selected such that the NTC device 502 will prevent delivery of energy to the electrode 25 when a prescribed temperature is reached. The prescribed temperature may be selected such that overheating of the jaw assembly is prevented. In other embodiments, the prescribed temperature may be a maximum temperature below which tissue heating is desired.

Using the NTC device 502 to control a delivery of energy to the electrode 25 is advantageous because it does not require use of a temperature sensor, nor does it require a separate processor to process (e.g., analyze) sensed parameters.

As shown in the figure, the NTC device 502 is secured at a location in the middle of the surgical instrument 9. In other embodiments, the NTC device 502 may be secured at other locations along the length of the surgical instrument 9, such as closer to, or at, the electrode 25. In further embodiments, the NTC device 502 may be secured near or at the energy source 30. In still further embodiments, the NTC device 502 may be coupled to the cable that connects the energy source 30 to the surgical instrument 9. In other embodiments, the NTC device 502 could also be located in the power supply, and different power supplies could include different NTCs (or several NTCs with the option to select them).

In any of the embodiments, the NTC device 502 may directly control (e.g., by placing the NTC device 502 directly in the circuit), or indirectly control (e.g., via relay or similar mechanism) the power circuit. In further embodiments, the NTC device 502 may also be used for allowing or preventing an additional power source (e.g., a RF source) to deliver power to the electrode 25. In some embodiments, the NTC device 502 may be implemented as a part of the electrode 25.

As illustrated in the above embodiments, the energy delivery control (e.g., provided by the control module 32, PTC device 500, or NTC device 502) is advantageous in that it controls delivery of energy to the electrode 25 in a desired manner, thereby achieving a good balance between quick tissue transection and excellent hemostasis. In particular, the energy delivery control ensures that an appropriate amount of thermal energy is applied to tissue to quickly transect and/or weld the tissue, while preventing too much thermal energy from being delivered such that the region of hemostasis (i.e., the tissue weld) is degraded. The energy delivery control is also advantageous in that it may be used to prevent over heating of the electrode 25 and/or other components of the jaw assembly, thereby preserving the integrity of the surgical instrument 9. In particular, by preventing the temperature of the components of the surgical instrument 9 from reaching excessive temperatures, component or mechanism failures (such as degradation of jaw members, melting of mechanical linkages, destruction of electrical circuit, etc.) are prevented.

In other embodiments, instead of using the control module 32, the PTC device 500, or NTC device 502, the surgical instrument 9 may provide a desired control of energy delivery using a proper design of the heating element (electrode 25). For example, the electrode 25 may be configured (e.g., by being sized, shaped, and/or constructed using proper materials) such that when a specific temperature is reached, the resistance of the electrode 25 increases to the point that current flowing through the electrode 25 is essentially zero, thereby resulting in the electrode 25 not substantially delivering additional energy (e.g., the additional energy being delivered by the electrode 25 is less than 10% of that initially provided by the electrode 25). This will "switch off" the heating temporarily until the residual heat dissipates (e.g., until the temperature has decreased below a certain point). When the heat is sufficiently dissipated, the resistance of the electrode 25 will change to a value that would allow for current to flow therethrough (due to the voltage potential provided by the energy source 30), thereby heating the electrode 25 again. This resistance "switch" is advantageous in that it can be used to toggle the heating of the electrode 25 to maintain the temperature at a specific point independent of user input (i.e., the user activates the actuator 15 at the handle 11 to switch the device "on," and the electrode 25 is automatically toggled "on" and "off" in response to temperature changes of the electrode 25 without further input by the user and without requiring a control module 32). In some cases, the electrode 25 may be configured so that it provides a desired rate of heating or cooling. This can be achieved because at a certain temperature of the electrode 25, the resistance change at the electrode 25 would alter the current flow therethrough. In any of the embodiments described herein, the electrode 25 may be configured to have a certain profile of resistance changes, thereby tailoring it to provide a specific heating profile.

Although the above embodiments have been described with reference to the surgical device 14 being a pair of jaws for clamping, cutting, and sealing vessel (e.g., saphenous vein, an artery, or any other vessel), in other embodiments, the surgical device 14 may have different configurations, and different functionalities. For example, in other embodiments, the surgical device 14 may be clip appliers or grasping jaws for grasping other types of tissues. Also, in any of the embodiments described herein, the surgical instrument 9 may be used in any endoscopic or open surgical procedure that requires transection of tissue. For example, in any of the embodiments described herein, the surgical instrument 9 may be provided as a part of a kit that includes a cannula. In some embodiments, the cannula has a distal end, a proximal end, and a lumen extending between the distal and proximal ends. The surgical instrument 9 is configured (e.g., sized and/or shaped) to be inserted into the lumen of the cannula. During use, the jaw assembly of the instrument 9 may extend out of the lumen at the distal end of the cannula. In some cases, the cannula may include one or more additional lumens, wherein one lumen may be configured to house an imaging device, such as an endoscope, and another lumen may be configured to house a light source or a fiber optic for delivering light.

Also, in any of the embodiments described herein, the jaw assembly at the distal end of the surgical instrument 9 does not need to include all of the features described herein. For example, in some embodiments, the jaw assembly does not include outer portions 50, 52. Instead, the jaw assembly includes one electrode strip (like the middle electrode portion 48 described above) for cutting or sealing tissue. Also, in other embodiments, the electrode(s)/operative element(s) may be on both jaws. For example, the outer portions 50, 52 (which may be considered as one or two electrodes) may be on one jaw, and the inner portion 48 (which may be considered as another electrode) may be on another jaw. Such configuration allows the welding element(s) to be on one jaw, and the cutting element to be on the other jaw. Furthermore, in other embodiments, the jaw 23 does not have the surface elevation 54. Instead, the jaw 23 may have a flat surface that is for contacting the inner and outer portions 48, 50, 52. In addition, in further embodiments, the jaws 21, 23 do not include the respective protrusions 60, 62. Instead, the cross section of the jaw 21/23 has a symmetrical configuration. In other embodiments, protrusion(s) are provided on both sides of the jaw assembly (e.g., one or more protrusions at the concave side of the jaw assembly, and one or more protrusions at the convex side of the jaw assembly). Such a configuration provides buffering on both sides of the jaw assembly, and allows for correct placement of the jaw assembly regardless of which side (the concave or convex side) of the jaw assembly is oriented towards the main vessel 142 during use. In further embodiments, instead of the curved configuration, the jaws could be straight. Also, in any of the embodiments described herein, instead of, or in addition to, using the jaw assembly for cutting and/or welding of vessel tissue, the jaw assembly may be used for transection of other types of tissue, such as fatty and connective tissue encountered during a vessel harvesting procedure or other procedures.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:
1. A surgical instrument comprising a jaw assembly comprising:
   a first jaw and a second jaw, each comprising opposing clamping surfaces for clamping tissue therebetween;
   a support structure on one of the first and second jaws;
   a single operative element, the single operative element comprising:
      a first thermal heating surface of one of the first and second jaws configured to seal tissue;
      a second thermal heating surface of one of the first and second jaws configured to seal tissue;
      a third thermal heating surface of one of the first and second jaws configured to sever tissue, wherein the third thermal heating surface is located between the first and second thermal heating surfaces when the first and second jaws are brought into proximity of one another; and
      a fourth thermal heating surface of one of the first and second jaws, wherein the fourth thermal heating surface extends from and laterally beyond a side of the jaw assembly to perform tissue spot cauterization by direct thermal conduction of heat emitted from the fourth thermal heating surface as a result of Joule heating;
   wherein the first, second, third and fourth heating surfaces electrically communicate with each other via a continuous electrical path; and
      wherein the first, second, third and fourth heating surfaces, when the single operative element is electrically coupled to a direct current source, heat up upon the delivery of direct current power between a first and second terminal of the direct current source.

2. The surgical instrument of claim 1, wherein the jaw assembly has a protrusion for abutment against a main vessel, and the protrusion is sized so that when the protrusion is abutted against the main vessel, the third thermal heating surface is automatically placed at a desired position relative to a side branch vessel.

3. The surgical instrument of claim 1, wherein the single operative element comprising the first, second, third and fourth thermal heating surfaces is only disposed on the first jaw.

4. The surgical instrument of claim 1, wherein the fourth thermal heating surface protrudes from a distal portion of a convex side of the first jaw, extending laterally beyond a side of the jaw assembly at a location between a distal end of the jaw assembly, and a proximal end of the jaw assembly.

5. The surgical instrument of claim 4, wherein an outer edge of the fourth thermal heating surface is generally smooth and continuous with an outer edge of the first or second thermal heating surfaces.

6. The surgical instrument of claim 4, wherein the second jaw comprises a raised portion that faces towards the first jaw.

7. The surgical instrument of claim 6, wherein the raised portion of the second jaw is in alignment with the third thermal heating surface.

8. The surgical instrument of claim 1, wherein the first, second and third thermal heating surfaces are continuous and configured as co-planar tissue contacting surfaces.

9. The surgical instrument of claim 1, wherein the first, second, third and fourth thermal heating surfaces are parts of a single thermal heating element disposed on the first jaw.

10. A surgical instrument comprising:
   a jaw assembly comprising a first jaw and a second jaw, wherein each of the first and second jaws comprises
      a proximal end extending from a body portion of the surgical instrument; and
      a distal end located distal to the proximal end;
   wherein the first jaw further comprises an operative element, the operative element comprising an inner portion provided with an inner surface for severing tissue positioned between the first and second jaws and an outer portion provided with a spot cauterization surface located lateral to a side of one of the first and second jaws, wherein a continuous electrical path exists between the inner portion and the outer portion, and the spot cauterization surface extends laterally with respect to and lengthwise along a distal portion of the side of the one of the first and second jaws, protruding laterally beyond the side of the one of the first and second jaws at a location between the distal end and proximal end of one of the first and second jaws, and when the first and second jaws are closed, the inner surface of the operative element is concealed by the second jaw and the spot cauterization surface is exposed for tissue spot cauterization by direct thermal conduction of Joule heat from the spot cauterization surface, and wherein with a flow of direct electrical current through the inner portion and outer portion, the spot cauterization surface heats to a first temperature due to a first current density of the flow of electrical current flowing in the outer portion, and the inner surface for severing tissue heats to a second temperature due to a second current density of the flow of direct electrical current flowing in the inner portion, wherein the second current density is higher than the first current density so that the second temperature is higher than the first temperature.

11. The surgical instrument of claim 10, wherein the operative element further comprises an inner surface for sealing tissue disposed on the first jaw and facing a surface of the second jaw and wherein a generally continuous gap is formed between a length of the inner surface for sealing tissue and the inner surface for severing tissue.

12. The surgical instrument of claim 10, wherein the first and second jaws are crescent shaped.

13. The surgical instrument of claim 12, wherein the spot cauterization surface protrudes from a convex side of the first jaw and has a generally smooth and continuous edge.

14. The surgical instrument of claim 12, wherein the first jaw further comprises a tapered lateral protrusion extending from a generally central region of the first jaw and tapering laterally towards a concave side of the first jaw.

15. The surgical instrument of claim 10, wherein a distal portion of the first jaw located along a concave portion of the first jaw is tapered at an angle of 10° to 40° relative to an adjoining side surface of the concave portion.

16. The surgical instrument of claim 10, wherein the spot cauterization surface extends laterally beyond an edge of the first jaw along only a portion of the first jaw in order to permit viewing along a longitudinal direction down the surgical instrument.

17. The surgical instrument of claim 10, wherein the operative element is an elongate thermal heating element.

18. The surgical instrument of claim 10, wherein the first temperature is sufficient to weld tissue and the second temperature is sufficient to sever tissue.

19. A surgical instrument comprising:
a handle;
an elongated body comprising a shaft extending from the handle; and
a jaw assembly comprising a first jaw and a second jaw, the jaw assembly configured to receive direct electrical current supplied by a direct current source, wherein each of the first and second jaws comprises a proximal end extending from the elongated body of the surgical instrument and a distal end located distal to the proximal end;
wherein the first jaw further comprises a first, second, and third thermal heating surface for applying thermal energy to tissue clamped between the first and second jaws, the first second and third heating surfaces extend lengthwise along the first jaw, are laterally spaced from each other along at least a substantial portion of the first jaw, and wherein the first, second, and third heating surfaces electrically communicate with each other via a continuous electrical path;
wherein one of the first and second jaws comprises a fourth thermal heating surface configured to provide thermal spot cauterization at a location lateral to a side of and longitudinally between the proximal end and distal end of one of the first and second jaws, wherein the fourth thermal heating surface is disposed to protrude laterally to that side, and beyond an edge, of the one of the first and second jaws so heat derived from the direct electrical current via Joule heating thermally conducts directly from the fourth heating surface to the location; and
wherein the fourth thermal heating surface is configured and positioned to allow a user to view along a length of the surgical instrument tissue during thermal spot cauterization and a target site to be received between the first and second jaws.

20. A method for tissue spot cauterization, wherein the method comprises the steps of:
positioning a surgical instrument along a tissue surface, wherein the surgical instrument comprises:
a first jaw and a second jaw, wherein the first jaw comprises
a proximal end extending from a body portion of the surgical instrument;
a distal end located distally of the proximal end; and
a clamping surface for clamping tissue between the first and second jaws;
wherein one of the first and second jaws comprises an inner severing surface and an outer sealing surface of conductive material disposed at the clamping surface for treating tissue clamped between the first and second jaws; and
wherein one of the first and second jaws comprises a thermal heating surface of the conductive material, at least a substantial portion of the thermal heating surface located proximal to the distal end of the one of the first and second jaws and extending laterally so as to laterally protrude beyond an edge of a side of the one of the first and second jaws, and wherein the inner severing surface, the outer sealing surface, and the thermal heating surface electrically communicate with each other via a continuos electrical path; and
thermally conducting heat energy directly from the second thermal heating surface to perform thermal spot cauterization at a location lateral to the side of the one of the first and second jaws;
wherein the heat energy is derived from a flow of direct electrical current through the conductive material.

21. A surgical instrument comprising:
a distal portion;
a proximal portion;
a jaw assembly extending from the distal portion, wherein the jaw assembly comprises a first jaw and a second jaw, each comprising a clamping surface for clamping tissue therebetween; and
wherein the first jaw comprises an operative planar element with a substantially flat surface for applying energy to the tissue when the tissue is clamped between the jaws, the flat surface of the operative element facing towards the clamping surface of the second jaw when the first and second jaws are brought into approximation to clamp the tissue between the first and second jaws, the operative element comprising:
an inner surface for severing tissue positioned between the first and second jaws and at least one outer surface for sealing the tissue positioned between the first and second jaws; and
a spot cauterization surface disposed laterally to protrude beyond a side of the jaw assembly, wherein the inner surface, the spot cauterization surface, and the outer surface electrically communicate with each other via a continuous electrical path, and wherein the spot cauterization surface is configured for spot cauterizing tissue placed in contact with the spot cauterization surface when the jaws are closed, and
when the first and second jaws are closed, the inner surface of the operative element is concealed by the second jaw and the spot cauterization surface is exposed so heat generated from direct electrical current flowing through the operative planar element via Joule heating conducts directly from the spot cauterization surface for tissue spot cauterization.

22. The surgical instrument of claim 21, wherein the spot cauterization surface is located on a convex side of the first jaw and is positioned to allow a user to view the spot cauterization surface from a proximal portion of the surgical instrument.

23. A surgical instrument comprising:
a distal portion;
a proximal portion;
a jaw assembly extending from the distal portion, wherein the jaw assembly comprises a first jaw and a second jaw, each comprising a clamping surface for clamping tissue therebetween; and
wherein the first jaw comprises an operative element for applying energy to the tissue when the tissue is clamped between the jaws, the operative element comprising
a surface for severing tissue positioned between the first and second jaws;
a surface for sealing tissue positioned between the first and second jaws; and
a spot cauterization surface disposed laterally to protrude beyond a side of the jaw assembly, wherein the spot cauterization surface is integral with the tissue sealing surface, electrically communicates with the tissue severing surface and the tissue sealing surface via a continuous electrical path, and is configured for spot cauterizing tissue placed in contact with the spot cauterization surface when the jaws are closed, wherein when direct electrical current flows through the operative element, the spot cauterization surface, the tissue severing surface, and the tissue sealing surface are heated together, and
when the first and second jaws are closed, the tissue sealing surface of the operative element is concealed by the second jaw and the spot cauterization surface is exposed so heat derived via Joule heating conducts directly from the spot cauterization surface for tissue spot cauterization.

* * * * *